(12) United States Patent
Tsukada et al.

(10) Patent No.: US 11,375,892 B2
(45) Date of Patent: Jul. 5, 2022

(54) METHOD OF PROCESSING OPTICAL COHERENCE TOMOGRAPHY (OCT) DATA AND OCT DATA PROCESSING APPARATUS

(71) Applicant: TOPCON CORPORATION, Tokyo (JP)

(72) Inventors: Hisashi Tsukada, Hachioji (JP); Atsushi Kubota, Itabashi-ku (JP); Yasufumi Fukuma, Wako (JP)

(73) Assignee: TOPCON CORPORATION, Tokyo (JP)

( * ) Notice: Subject to any disclaimer, the term of this patent is extended or adjusted under 35 U.S.C. 154(b) by 0 days.

(21) Appl. No.: 16/916,154

(22) Filed: Jun. 30, 2020

(65) Prior Publication Data
US 2021/0000338 A1    Jan. 7, 2021

(30) Foreign Application Priority Data

| Jul. 2, 2019 | (JP) | JP2019-123431 |
| Jul. 2, 2019 | (JP) | JP2019-123437 |
| Jul. 11, 2019 | (JP) | JP2019-129315 |

(51) Int. Cl.
*G01B 9/02* (2022.01)
*A61B 3/10* (2006.01)
(Continued)

(52) U.S. Cl.
CPC .............. *A61B 3/102* (2013.01); *A61B 3/0025* (2013.01); *A61B 3/12* (2013.01); *A61B 5/0066* (2013.01);
(Continued)

(58) Field of Classification Search
CPC ......... A61B 3/102; A61B 3/0025; A61B 3/12; A61B 5/0066; G06T 7/32; G06T 3/0068;
(Continued)

(56) References Cited

U.S. PATENT DOCUMENTS

| 7,884,945 B2 | 2/2011 | Srinivasan et al. |
| 8,405,834 B2 | 3/2013 | Srinivasan et al. |

(Continued)

FOREIGN PATENT DOCUMENTS

| JP | 6230023 B2 | 11/2017 |
| JP | 6276943 B2 | 2/2018 |

OTHER PUBLICATIONS

Shuliang Jiao, "Simultaneous acquisition of sectional and fundus ophthalmic images with spectral-domain optical coherence tomography", Bascom Palmer Eye Institute, University of Miami School of Medicine, 1638 NW 10th Ave, Miami, FL 33136, Jan. 24, 2005 / vol. 13, No. 2 / Optics Express 444, 9 pp.

(Continued)

*Primary Examiner* — Tarifur R Chowdhury
*Assistant Examiner* — Jonathon Cook
(74) *Attorney, Agent, or Firm* — Xsensus LLP

(57) ABSTRACT

An exemplary aspect is a method of processing data acquired by applying an optical coherence tomography (OCT) scan to a sample. The method includes preparing a three dimensional data set acquired from a sample, creating a two dimensional map based on representative intensity values of a plurality of pieces of A-scan data included in the three dimensional data set, placing the three dimensional data set based on the two dimensional map, and executing a process based on at least a partial data set of the three dimensional data set on which placement based on the two dimensional map has been performed.

20 Claims, 23 Drawing Sheets

(51) Int. Cl.
*A61B 5/00* (2006.01)
*G01B 9/02091* (2022.01)
*G06T 7/32* (2017.01)
*A61B 3/00* (2006.01)
*A61B 3/12* (2006.01)
*G06T 3/00* (2006.01)
*G06T 3/20* (2006.01)
*G06T 3/60* (2006.01)

(52) U.S. Cl.
CPC ..... *G01B 9/02083* (2013.01); *G01B 9/02091* (2013.01); *G06T 3/0068* (2013.01); *G06T 3/20* (2013.01); *G06T 3/60* (2013.01); *G06T 7/32* (2017.01); *G06T 2200/04* (2013.01); *G06T 2207/10101* (2013.01); *G06T 2207/20212* (2013.01); *G06T 2207/30041* (2013.01)

(58) Field of Classification Search
CPC ......... G06T 3/20; G06T 3/60; G06T 2200/04; G06T 2207/10101; G06T 2207/30041; G01B 9/02083; G01B 9/02091
See application file for complete search history.

(56) References Cited

U.S. PATENT DOCUMENTS

| | | | |
|---|---|---|---|
| 2007/0070295 A1* | 3/2007 | Tsukada | A61B 3/102 351/206 |
| 2007/0216909 A1 | 9/2007 | Everett et al. | |
| 2010/0208201 A1 | 8/2010 | Knighton et al. | |
| 2011/0134394 A1 | 6/2011 | Srinivasan et al. | |
| 2013/0003077 A1* | 1/2013 | Suehira | G01B 9/02087 356/479 |
| 2013/0301001 A1 | 11/2013 | Carnevale | |
| 2014/0293289 A1 | 10/2014 | Reisman | |
| 2015/0042952 A1* | 2/2015 | Uchida | G06T 7/11 351/206 |
| 2016/0198940 A1 | 7/2016 | Shibutani et al. | |
| 2017/0209037 A1* | 7/2017 | Sumiya | A61B 3/1025 |
| 2018/0003479 A1* | 1/2018 | Tomatsu | G01B 9/02087 |
| 2019/0000313 A1 | 1/2019 | Sadda et al. | |
| 2019/0150729 A1 | 5/2019 | Huang et al. | |

OTHER PUBLICATIONS

Extended European Search Report dated Nov. 20, 2020, issued in corresponding European Patent Application No. 20182149.3.
Extended European search report dated Mar. 5, 2021, in corresponding European patent Application No. 20182150.1, 15 pages.
Akihito Uji et al., "Impact of Multiple En Face Image Averaging on Quantitative Assessment from Optical Coherence Tomography Angiography Images", American Academy of Ophthalmology, Ophthalmology, vol. 124, No. 7, Jul. 2017, pp. 944-952.
M. Pohit et al., "Image registration under translation and rotation in two-dimensional planes using Fourier slice theorem", Applied Optics, Optical Society of America, vol. 54, No. 14, May 10, 2015, pp. 4514-4519.
Partial European search report dated Nov. 24, 2020, in corresponding European patent Application No. 20182150.1, 13 pages.
Partial European search report dated Dec. 2, 2020, in corresponding European patent Application No. 20182152.7, 11 pages.
Zhang et al., "Adaptive Optics with Combined Optical Coherence Tomography and Scanning Laser Ophthalmoscopy for in vivo mouse retina imaging", Proc. of SPIE, vol. 10474, Feb. 22, 2018, pp. 1047427-1-1047427-9, total 9 pages, XP060100531.
Extended European search report dated Jan. 17, 2022, in corresponding European patent Application No. 21200117.6.

* cited by examiner

METHOD OF PROCESSING OPTICAL COHERENCE TOMOGRAPHY (OCT) DATA AND OCT DATA PROCESSING APPARATUS

CROSS-REFERENCE TO RELATED APPLICATIONS

This application is based upon and claims the benefit of priority from Japanese Patent Applications No. 2019-123431, filed Jul. 2, 2019, No. 2019-123437, filed Jul. 2, 2019, and No. 2019-129315, filed Jul. 11, 2019; the entire contents of each are incorporated herein by reference.

FIELD

The present disclosure relates generally to a method of processing optical coherence tomography (OCT) data and an OCT data processing apparatus.

BACKGROUND

OCT is an imaging technique capable of representing a light scattering medium at a resolution of micrometer level or less, and is used for medical imaging, nondestructive testing, and the like. OCT is a low-coherence-interferometry-based technique and typically utilizes near infrared light to ensure the reaching depth of the light into a sample of a scattering medium.

U.S. Pat. No. 7,884,945 discloses a method of processing an OCT data set represented as a function of optical depths that is obtained by a measurement of backscattering or back reflection in order to acquire OCT data efficiently and to acquire OCT data from a specific region of a sample accurately and in a short time. The method includes a step of analyzing an OCT data set to identify landmark region data of at least the first subset, a step of placing the OCT data set based on the landmark region data, and a step of processing at least the second subset of the OCT data set based on the correspondence between the OCT data set and the landmark region data.

Further, U.S. Pat. No. 8,405,834 discloses a method for monitoring disease progression. The method includes a step of acquiring an OCT survey scan data set represented as a function of optical depths that is obtained by a measurement of backscattering or back reflection, a step of analyzing the survey scan data set to identify a landmark region, a step of assigning a location in the sample or a location relating to a fixed position to an element of the survey scan data set to register part of the survey scan data set representing at least part of a diseased or affected tissue region relating to the landmark region, and a step of monitoring the changes in the diseased or affected tissue region at different points in time.

SUMMARY

An object of the present disclosure is to improve the efficiency of OCT data processing.

Some exemplary aspects relate to a method of processing data acquired by applying an optical coherence tomography (OCT) scan to a sample. The method includes: preparing a three dimensional data set acquired from a sample; creating a two dimensional map based on representative intensity values of a plurality of pieces of A-scan data included in the three dimensional data set; placing the three dimensional data set based on the two dimensional map; and executing a process based on at least a partial data set of the three dimensional data set on which placement based on the two dimensional map has been performed.

Any of the following optional aspects may be combined with an OCT imaging method of some exemplary aspects: the process includes an analysis process; the process includes an evaluation process based on data obtained by the analysis process; the process includes setting of a partial data set to which the analysis process is applied; the process includes setting of an area to which an examination for the sample is applied; the process includes setting of a partial data set to which an imaging process is applied; preparing examination data acquired from the sample by an examination different from OCT, and the process includes a comparison process between the examination data and at least part of the three dimensional data set.

Some exemplary aspects relate to a method of processing data acquired by applying an optical coherence tomography (OCT) scan to a sample. The method includes: preparing a first three dimensional data set and a second three dimensional data set acquired from a sample; creating a first two dimensional map based on representative intensity values of a plurality of pieces of A-scan data included in the first three dimensional data set; creating a second two dimensional map based on representative intensity values of a plurality of pieces of A-scan data included in the second three dimensional data set; and executing a process based on at least one of at least a first partial data set of the first three dimensional data set and at least a second partial data set of the second three dimensional data set, based on the first two dimensional map and the second two dimensional map.

Any of the following optional aspects may be combined with an OCT imaging method of some exemplary aspects: the process includes registration between the at least the first partial data set and the at least the second partial data set via registration between the first two dimensional map and the second two dimensional map; the process includes adjustment of an area to which an OCT scan for the sample is applied via registration between the first two dimensional map and the second two dimensional map; the adjustment is sequentially performed by sequentially processing three dimensional data sets sequentially acquired from the sample; the registration between the first two dimensional map and the second two dimensional map includes an image correlation calculation the image correlation calculation is performed to determine a positional difference amount between the first two dimensional map and the second two dimensional map, and the registration between the first two dimensional map and the second two dimensional map is performed based on the positional difference amount; the positional difference amount includes at least one of a translation amount and a rotation amount; the first three dimensional data set and the second three dimensional data set are acquired from mutually different three dimensional regions of the sample, and the process includes composition of first image data generated from the at least the first partial data set and second image data generated from the at least the second partial data set via registration between the first two dimensional map and the second two dimensional map; the process includes an analysis process; the process includes an evaluation process based on data obtained by the analysis process; the process includes setting of a partial data set to which the analysis process is applied; preparing a plurality of three dimensional data sets respectively corresponding to a plurality of different time points, the plurality of three dimensional data sets including the first three dimensional data set and the second three dimensional data set, and the analysis process includes a process of determining a time course of a parameter value.

Some exemplary aspects relate to an optical coherence tomography (OCT) apparatus. The OCT apparatus includes: an OCT scanner that acquires a three dimensional data set by applying an OCT scan to a sample; a map creating unit that creates a two dimensional map based on representative intensity values of a plurality of pieces of A-scan data included in the three dimensional data set; a placing unit that performs placement of the three dimensional data set based on the two dimensional map; and a process executing unit that executes a process based on at least a partial data set of the three dimensional data set on which the placement has been performed.

Some exemplary aspects relate to an optical coherence tomography (OCT) apparatus. The OCT apparatus includes: an OCT scanner that acquires a first three dimensional data set and a second three dimensional data set by applying OCT scans to a sample; a map creating unit that creates a first two dimensional map based on representative intensity values of a plurality of pieces of A-scan data included in the first three dimensional data set, and creates a second two dimensional map based on representative intensity values of a plurality of pieces of A-scan data included in the second three dimensional data set; and a process executing unit that executes a process based on at least one of at least a first partial data set of the first three dimensional data set and at least a second partial data set of the second three dimensional data set, based on the first two dimensional map and the second two dimensional map.

Some exemplary aspects relate to a method of controlling an optical coherence tomography (OCT) apparatus including a processor and an OCT scanner that applies an OCT scan to a sample. The method includes: controlling the OCT scanner to acquire a three dimensional data set from a sample; controlling the processor to create a two dimensional map based on representative intensity values of a plurality of pieces of A-scan data included in the three dimensional data set; controlling the processor to perform placement of the three dimensional data set based on the two dimensional map; and controlling the processor to execute a process based on at least a partial data set of the three dimensional data set on which the placement has been performed.

Some exemplary aspects relate to a method of controlling an optical coherence tomography (OCT) apparatus including a processor and an OCT scanner that applies an OCT scan to a sample. The method includes: controlling the OCT scanner to acquire a first three dimensional data set and a second three dimensional data set from a sample; controlling the processor to create a first two dimensional map based on representative intensity values of a plurality of pieces of A-scan data included in the first three dimensional data set, and create a second two dimensional map based on representative intensity values of a plurality of pieces of A-scan data included in the second three dimensional data set; and controlling the processor to execute a process based on at least one of at least a first partial data set of the first three dimensional data set and at least a second partial data set of the second three dimensional data set, based on the first two dimensional map and the second two dimensional map.

Some exemplary aspects relate to an optical coherence tomography (OCT) data processing apparatus. The OCT data processing apparatus includes: a receiving unit that receives a three dimensional data set acquired by applying an OCT scan to a sample; a map creating unit that creates a two dimensional map based on representative intensity values of a plurality of pieces of A-scan data included in the three dimensional data set; a placing unit that performs placement of the three dimensional data set based on the two dimensional map; and a process executing unit that executes a process based on at least a partial data set of the three dimensional data set on which the placement has been performed.

Some exemplary aspects relate to an optical coherence tomography (OCT) data processing apparatus. The OCT data processing apparatus includes: a receiving unit that receives a first three dimensional data set and a second three dimensional data set acquired by applying OCT scans to a sample; a map creating unit that creates a first two dimensional map based on representative intensity values of a plurality of pieces of A-scan data included in the first three dimensional data set, and creates a second two dimensional map based on representative intensity values of a plurality of pieces of A-scan data included in the second three dimensional data set; and a process executing unit that executes a process based on at least one of at least a first partial data set of the first three dimensional data set and at least a second partial data set of the second three dimensional data set, based on the first two dimensional map and the second two dimensional map.

Some exemplary aspects relate to a method of controlling an optical coherence tomography (OCT) data processing apparatus including a processor. The method includes: controlling the processor to receive a three dimensional data set acquired by applying an OCT scan to a sample; controlling the processor to create a two dimensional map based on representative intensity values of a plurality of pieces of A-scan data included in the three dimensional data set; controlling the processor to perform placement of the three dimensional data set based on the two dimensional map; and controlling the processor to execute a process based on at least a partial data set of the three dimensional data set on which the placement has been performed.

Some exemplary aspects relate to a method of controlling an optical coherence tomography (OCT) data processing apparatus including a processor. The method includes: controlling the processor to receive a first three dimensional data set and a second three dimensional data set acquired by applying OCT scans to a sample; controlling the processor to create a first two dimensional map based on representative intensity values of a plurality of pieces of A-scan data included in the first three dimensional data set, and create a second two dimensional map based on representative intensity values of a plurality of pieces of A-scan data included in the second three dimensional data set; and controlling the processor to execute a process based on at least one of at least a first partial data set of the first three dimensional data set and at least a second partial data set of the second three dimensional data set, based on the first two dimensional map and the second two dimensional map.

Some exemplary aspects relate to a program that causes a computer to execute any one of the methods of the exemplary aspects.

Some exemplary aspects relate to a computer-readable non-transitory recording medium storing any one of the programs of the exemplary aspects.

According to some exemplary aspects, improvements on the efficiency of OCT data processing may be achieved.

DETAILED DESCRIPTION

Figure 1:
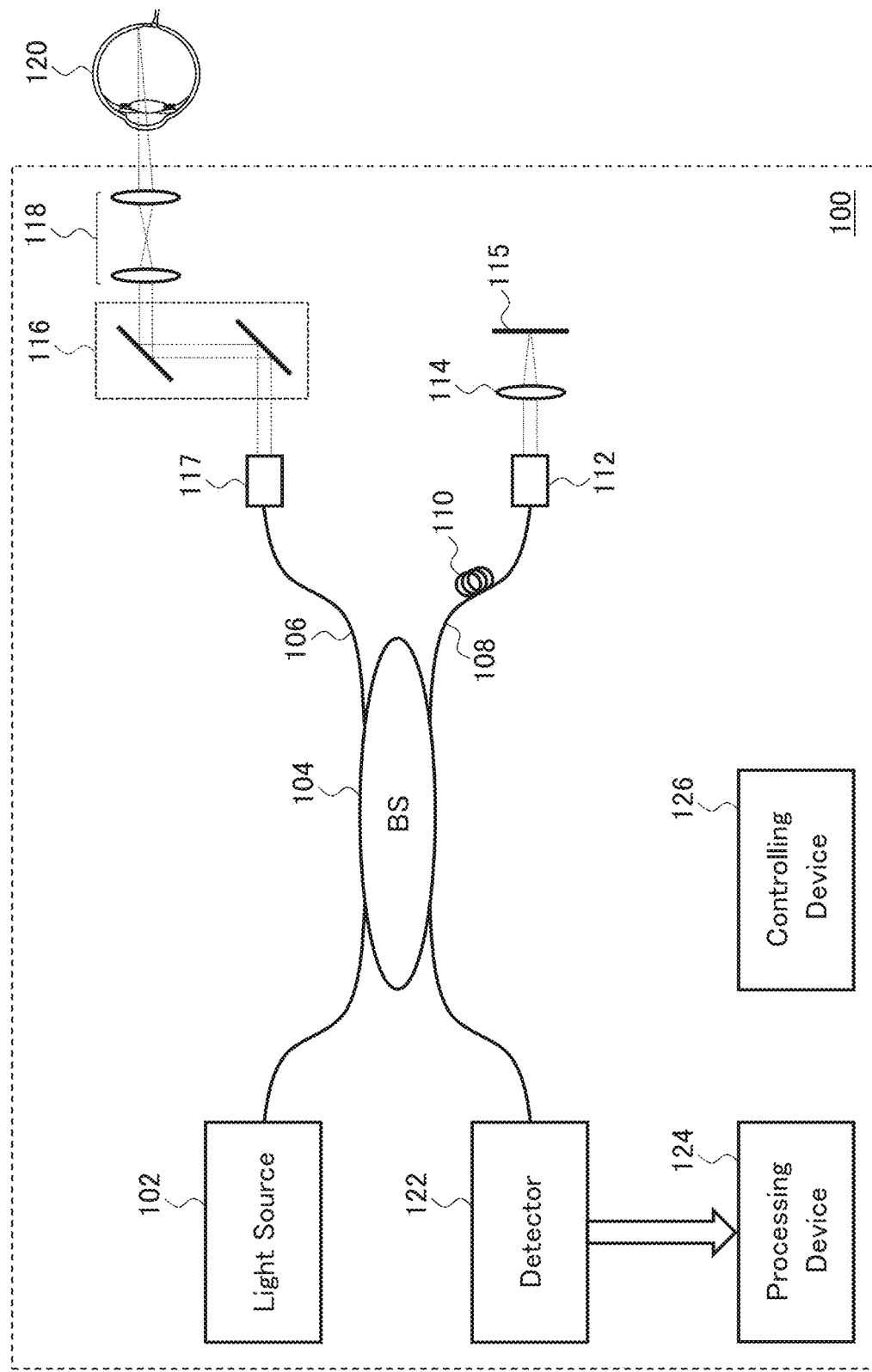
FIG. 1 is a schematic diagram illustrating the configuration of the ophthalmic apparatus (OCT apparatus) according to the exemplary aspect.

Some exemplary aspects of embodiments are described below. Note that any of the matters disclosed in the documents cited in the present specification may be incorporated into the exemplary aspects. Also, any matters relating to known technologies or known techniques may be incorporated into the exemplary aspects.

Some exemplary aspects relate to a technique (OCT data processing method) for processing a three dimensional data set acquired by applying an OCT scan to a three dimensional region of a sample. Some exemplary aspects include a process of creating a two dimensional map from a plurality of pieces of A-scan data included in the three dimensional data set.

Furthermore, the three dimensional data set is placed (or, located or positioned) based on the two dimensional map. Such placement (or, locating, positioning or registration) typically includes any one or both of the following processes: a process of determining the correspondence (or positional relationship) between the three dimensional data set and the sample region; and a process of determining the correspondence (or positional relationship) between the three dimensional data set and another three dimensional data set.

In addition, processing is executed based on at least part of the three dimensional data set on which the placement based on the two dimensional map has been performed. This processing is executed, for example, on one or two or more three dimensional data sets, and may include any of the followings: analysis; setting of an analysis area; evaluation of analysis data; setting of an evaluation area; setting of an examination area; setting of an imaging area; and comparison with another examination data. Here, the another examination data compared may be any one or more of the followings: data acquired by applying OCT scanning to the same sample; data acquired by applying an examination different from OCT scanning to the same sample; data acquired by applying OCT scanning to one or more other samples; and data acquired by applying an examination different from OCT scanning to one or more other samples.

Some other exemplary aspects relate to a technique (OCT data processing method) for processing the first three dimensional data set and the second three dimensional data set acquired by applying OCT scans respectively to the first three dimensional region and the second three dimensional region of a sample. The exemplary aspects include a process of creating the first two dimensional map from a plurality of pieces of A-scan data included in the first three dimensional data set, and a process of creating the second two dimensional map from a plurality of pieces of A-scan data included in the second three dimensional data set.

Furthermore, based on the first two dimensional map and the second two dimensional map, processing based on at least part of the first three dimensional data set and/or at least part of the second three dimensional data set is executed. The processing may include, for example, any of the followings: registration; tracking; panoramic OCT imaging (or, mosaic OCT imaging or montage OCT imaging); analysis (e.g., static analysis or dynamic analysis (e.g., time series analysis, time course analysis)); setting of an analysis area; evaluation of analysis data; setting of an evaluation area; setting of an examination area; setting of an imaging area; and comparison with another examination data.

Some exemplary aspects relate to a modality apparatus/device (including at least an OCT apparatus) that can realize any of the exemplary OCT data processing methods described above, and have a function of acquiring a three dimensional data set by applying an OCT scan to a sample. Further, some exemplary aspects relate to a method of controlling such an OCT apparatus.

Some exemplary aspects relate to an information processing apparatus (an OCT data processing apparatus) that can realize any of the exemplary OCT data processing methods described above, and have a function of receiving OCT data (a three dimensional data set) acquired from a sample. Further, some exemplary aspects relate to a method of controlling such an OCT data processing apparatus.

Some exemplary aspects relate to a program that causes a computer to execute any of the exemplary methods (i.e., any of the OCT data processing methods or controlling methods) described above. Here, the computer may be a modality apparatus/device that includes at least a computer and an OCT apparatus. In addition, some exemplary aspects relate to a computer-readable non-transitory recording medium on which such a program is recorded.

In some exemplary aspects, a "processor" is, for example, a circuit (circuitry) such as a central processing unit (CPU), a graphics processing unit (GPU), an application specific integrated circuit (ASIC), a programmable logic device (e.g., a simple programmable logic device (SPLD)), a complex programmable logic device (CPLD), a field programmable gate array (FPGA), or the like. The processor provides some examples for realizing desired functions, for example, by reading out and executing a program stored in a storage circuit or a storage device.

The type of OCT applicable to some exemplary aspects is optional, and is typically swept source OCT or spectral domain OCT. However, any other types of OCT may be employed.

Swept source OCT is an imaging technique performed by splitting light emitted from a wavelength tunable light source into measurement light and reference light, superposing the return light of the measurement light returned from the sample with the reference light to generate interference light, detecting the interference light with a photodetector, and applying Fourier transform and other processes to the detected data acquired according to the wavelength sweeping and the measurement light scanning.

Spectral domain OCT is an imaging technique performed by splitting light emitted from a low coherence light source (broadband light source) into measurement light and reference light, superposing the return light of the measurement light returned from the sample with the reference light to generate interference light, detecting the interference light using a spectrometer to obtain the spectral distribution thereof, and applying Fourier transform and other processes to the spectral distribution detected.

In brief, swept source OCT is an OCT technique of acquiring the spectral distribution of the interference light by time division, and spectral domain OCT is an OCT technique of acquiring the spectral distribution of the interference light by space division.

Types other than such Fourier domain OCT include time domain OCT and en-face OCT (or full field OCT). Time domain OCT introduces mechanical and sequential scanning in the axial direction (Z direction). En-face OCT provides two dimensional imaging of the XY plane orthogonal to the Z direction.

The exemplary aspects described below may be used in ophthalmic imaging, analysis, measurement, evaluation and the like. However, some exemplary aspects may be used in any fields other than ophthalmology such as medical fields other than ophthalmology (e.g., dermatology, dentistry, surgery) and industrial fields (e.g., nondestructive testing).

First Aspect Example

Figure 2:
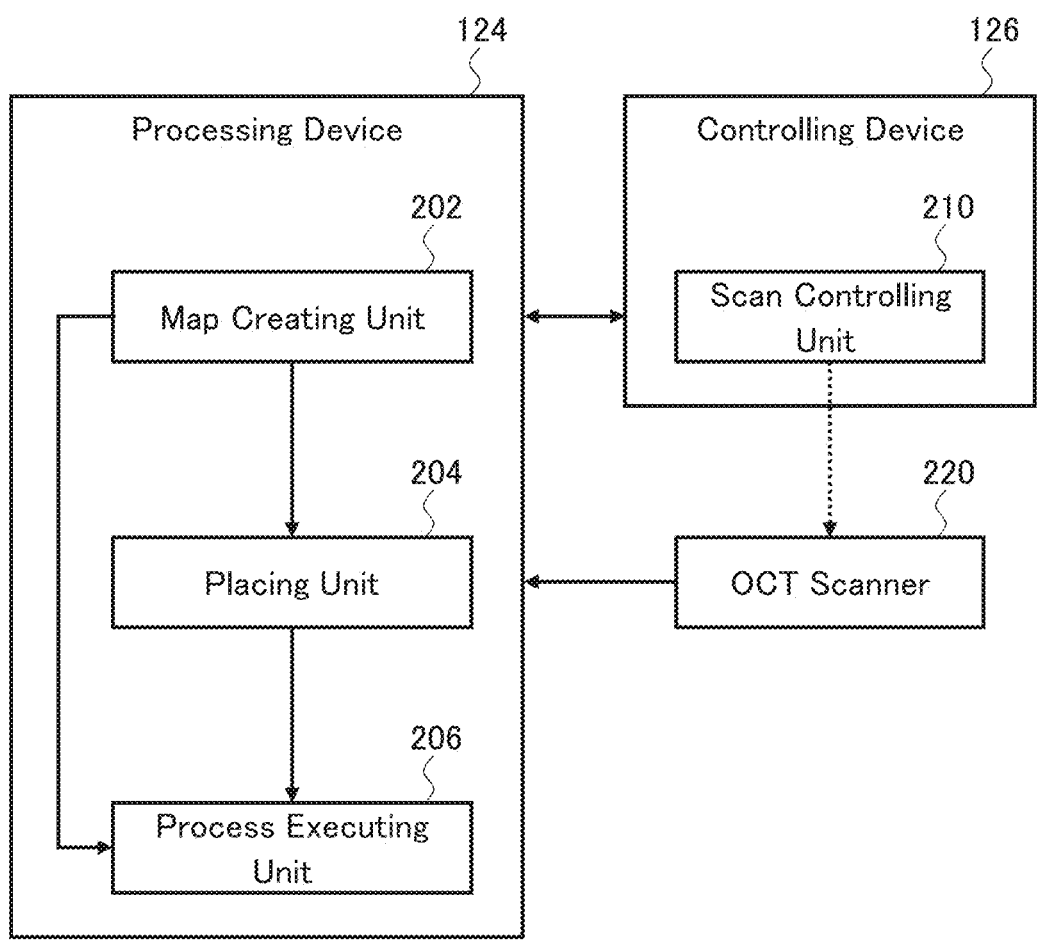
FIG. 2 is a schematic diagram illustrating the configuration of the ophthalmic apparatus according to the exemplary aspect.

FIGS. 1 and 2 show the configuration of the OCT apparatus (ophthalmic apparatus) 100 according to one exemplary aspect. The ophthalmic apparatus 100 provides OCT data processing in addition to OCT imaging.

More specifically, the ophthalmic apparatus 100 is configured to acquire a three dimensional data set by applying an OCT scan targeting a three dimensional region of a sample (the eye 120). Here, the three dimensional region is set to an arbitrary area. Further, taking eye movements and the like into consideration, it is not necessary that a region to which an OCT scan targeting a three dimensional region is actually applied coincides with the targeted three dimensional region. However, a region that substantially coincides with the targeted three dimensional region may be scanned using techniques such as fixation and tracking.

In addition, the ophthalmic apparatus 100 is configured to create a two dimensional map based on representative intensity values respectively of a plurality of pieces of A-scan data included in the three dimensional data set acquired from the sample. Here, the three dimensional data set is data before being subjected to an imaging process (e.g., Fourier transform). The three dimensional data set typically consists of a plurality of pieces of A-scan data arranged in a two dimensional manner on the XY plane. Each piece of A-scan data is a spectral intensity distribution (e.g., distribution data representing the relationship between wave numbers and intensities). Note that application of Fourier transform etc. to A-scan data yields A-scan image data representing a reflection intensity distribution (backscattering intensity distribution) along the Z direction. The processing of creating such a two dimensional map from a three dimensional data set may include, for example, the processing disclosed in Japanese Patent No. 6,230,023 (US Patent Application Publication No. 2014/0293289).

Furthermore, the ophthalmic apparatus 100 is configured to perform placement of the three dimensional data set based on the two dimensional map. The placement may include one of the following processes, for example: a process of determining a correspondence (a positional relationship) between the three dimensional data set and a region of the sample; a process of determining a correspondence (a positional relationship) between the three dimensional data set and another three dimensional data set; and a process of determining a correspondence (a positional relationship) between the three dimensional data set and examination data. The positional relationship determination may include any of the followings, for example: an association of coordinates of the three dimensional data set with a predetermined identifier (the name of a site, etc.); an association of respective coordinates with each other; an association of respective coordinate systems in which concerned objects are defined; and representation of concerned objects by a common coordinate system.

One example may determine the positional relationship between a specific site of the eye 120 and the three dimensional data set. The specific site of the eye 120 may be, for example, any of the followings: lesion; blood vessel; optic nerve head; macula; sub-tissue of eye fundus (e.g., inner limiting membrane, nerve fiber layer, ganglion cell layer, inner plexiform layer, inner nuclear layer, outer plexiform layer, outer nuclear layer, external limiting membrane, photoreceptor layer, retinal pigment epithelium layer, Bruch membrane, choroid, sclera, etc.); sub-tissue of cornea (e.g., corneal epithelium, Bowman's membrane, corneal stroma, Dua's layer, Descemet's membrane, corneal endothelium, etc.); iris; crystalline lens; Zinn's zonule; ciliary body; vitreous body; and other ocular tissues. As a typical example, part of the three dimensional data set corresponding to the optic nerve head is identified, or part of the three dimensional data set corresponding to the retinal pigment epithelium layer is identified.

Another example may determine the positional relationship between the three dimensional data set of the eye 120 and another three dimensional data set (e.g., OCT data acquired from the eye 120 or another eye). As an example, the positional relationship between two three dimensional data sets may be determined so that respective regions corresponding to a common specific site coincide with each other. For example, the positional relationship between two three dimensional data sets may be determined so that a region of one three dimensional data set corresponding to the optic nerve head coincides with a region of the other three dimensional data set corresponding to the optic nerve head. Alternatively, the positional relationship between two three dimensional data sets may be determined so that the positional relationship between respective regions corresponding to mutually different specific sites coincides with that between the respective specific sites. For example, the positional relationship between two three dimensional data sets may be determined so that the positional relationship between a region of the three dimensional data set corresponding to the optic nerve head and a region of the other three dimensional data set corresponding to the macula coincides with the positional relationship between the optic nerve head and the macula.

In yet another example, the positional relationship between the three dimensional data set of the eye 120 and examination data may be determined. The examination data is data acquired by applying an examination to the eye 120 or another eye). For example, the positional relationship between a three dimensional data set of the fundus of the eye 120 and sensitivity distribution data obtained by the visual field examination (perimetry) of the eye 120 (or an electroretinogram (EGR) obtained by an electrophysiological examination) may be determined. Alternatively, the positional relationship between a three dimensional data set of the fundus of the eye 120 and pre-created standard data (normative data) of retinal layer thickness distribution may be determined.

In addition, the ophthalmic apparatus 100 is configured to execute processing based on part or all of the three dimensional data set on which the placement has been performed. This processing is executed, for example, on one or two or more three dimensional data sets, and may include any of the followings: analysis; setting of an analysis area; evaluation of analysis data; setting of an evaluation area; setting of an examination area; setting of an imaging area; and comparison with another examination data. A part of the three dimensional data set is referred to as a partial data set. For convenience of description, a partial data set (or, sub-data set, data subset, or the like) may be the entire three dimensional data set.

Data that can be utilized in the processing of the partial data set may include any of the followings: (1) a three dimensional region of the eye 120; (2) a three dimensional data set; (3) a two dimensional map; (4) data generated from any of (1) to (3); (5) a combination of any two or more of (1) to (4); and (6) data generated from a combination of any two or more of (1) to (5).

As shown in FIG. 1, the ophthalmic apparatus 100 includes the light source 102 that generates a light beam. The light source 102 is, for example, a broadband light source or a wavelength tunable light source. The beam splitter (BS) 104 splits a light beam emitted from the light source 102 into two light beams known as a sample light beam (measurement light) and a reference light beam (reference light). In other words, the beam splitter 104 directs part of the light beam emitted from the light source 102 to the sample arm 106 and another part to the reference arm 108.

The reference arm 108 includes the polarization controller 110 and the collimator 112. The polarization controller 110 is used for regulating the reference light beam, for example, for maximizing the interference efficiency. The collimator 112 outputs the reference light beam as a collimated light beam (parallel light beam). The reference light beam output from the collimator 112 is converted into a convergent light beam by the lens 114 and projected onto the reflecting mirror 115. The reference light beam reflected by the reflecting mirror 115 returns to the beam splitter 104 through the reference arm 108. The lens 114 and the reflecting mirror 115 are movable together, whereby the distance from the collimator 112 is changed (in other words, the path length of the reference light beam is changed).

The sample arm 106 guides the sample light beam via the collimator 117, the two dimensional scanner 116, and one or more objective lenses 118, and projects the sample light beam onto the eye 120 as a sample. The two dimensional scanner 116 is, for example, a galvano mirror scanner or a micro electro mechanical systems (MEMS) scanner. The return light of the sample light beam projected on the eye 120 returns to the beam splitter 104 through the sample arm 106. The two dimensional scanner 116 enables OCT scanning on a three dimensional region of the eye 120.

The beam splitter 104 generates an interference light beam by superposing the return light of the reference light beam and the return light of the sample light beam with one another. The interference light beam is guided to the detector 122 and detected by it. With this, the echo time delay of the light is measured from the interference spectrum.

The detector 122 generates a plurality of output sets, based on the composition (superposition) of the return light of the sample light beam supplied from the sample arm 106 and the return light of the reference light beam supplied from the reference arm 108. The result of the composition is interferogram data. For example, the output sets generated by the detector 122 may respectively correspond to light intensities received at different wavelengths output from the light source 102. When the sample light beam is projected sequentially to XY positions by the two dimensional scanner 116, the light intensities detected include information, for the XY positions, on reflection intensity distributions (back-scattering intensity distributions) from the inside region of the eye 120 along the depth direction (Z direction).

A three dimensional data set is obtained in the above-described manner. The three dimensional data set includes a plurality of pieces of A-scan data respectively corresponding to the XY positions. Each piece of A-scan data represents a spectral intensity distribution at a corresponding XY position. The three dimensional data set acquired by the detector 122 is sent to the processing device 124.

The processing device 124 is configured to execute the followings, for example: a process of creating a two dimensional map based on the three dimensional data set; a process of placing the three dimensional data set based on the two dimensional map; and a process based on a partial data set of the three dimensional data set to which the placement has already been applied. The processing device 124 includes a processor that operates according to a processing program. Some specific examples of the processing device 124 will be described later.

The controlling device 126 executes control of each part of the ophthalmic apparatus 100. For example, the controlling device 126 is configured to perform various controls to apply an OCT scan to a preset region of the eye 120. The controlling device 126 includes a processor that operates according to a control program. Some specific examples of the controlling device 126 will be described later.

Although not shown in the drawings, the ophthalmic apparatus 100 may further include a display device, an operation device, a communication device, and other elements.

The processing device 124 and the controlling device 126 will be described in more detail with referring to FIG. 2. The processing device 124 includes the map creating unit 202, the placing unit 204, and the process executing unit 206. The controlling device 126 includes the scan controlling unit 210.

The OCT scanner 220 shown in FIG. 2 applies an OCT scan to the sample (the eye 120). The OCT scanner 220 of the present aspect includes, for example, the group of optical elements shown in FIG. 1, namely, the light source 102, the beam splitter 104, the sample arm 106 (the collimator 117, the two dimensional scanner 116, the objective lens 118, etc.), the reference arm 108 (the collimator 112, the lens 114, the reflecting mirror 115, etc.), and the detector 122. Some exemplary aspects may introduce OCT scanners having other configurations.

The controlling device 126 executes control of each part of the ophthalmic apparatus 100. Control relating to OCT scanning, among various kinds of control, is performed by the scan controlling unit 210. The scan controlling unit 210 of the present aspect is configured to perform control for the OCT scanner 220. For example, the scan controlling unit 210 of the present aspect may be configured to perform control for the light source 102, control for the two dimensional scanner 116, and movement control for the lens 114 and the reflecting mirror 115. The scan controlling unit 210 includes a processor that operates according to a scan controlling program.

The processing device 124 executes various kinds of data processing such as computation, operation, calculation, analysis, measurement, and image processing. The map creating unit 202, the placing unit 204, and the process executing unit 206 respectively perform the three processes described above, namely, the creation of a two dimensional map based on the three dimensional data set, the placement of the three dimensional data set based on the two dimensional map, and the process based on a partial data set of the three dimensional data set on which the placement has been performed.

The map creating unit 202 includes a processor that operates according to a map creating program. The placing unit 204 includes a processor that operates according to a placing program. The process executing unit 206 includes a processor that operates according to a process executing program.

The map creating unit 202 receives three dimensional data acquired from the eye 120 by an OCT scan, from the OCT scanner 220. The OCT scan is performed by the OCT scanner 220 under the control of the scan controlling unit 210, targeting a preset three dimensional region of the eye 120. With the OCT scan, a three dimensional data set is collected and acquired, and supplied to the map creating unit 202.

The map creating unit 202 creates a two dimensional map based on representative intensity values respectively of a plurality of pieces of A-scan data included in the three dimensional data set. The three dimensional data set is, for example, data before being subjected to the imaging process (e.g., Fourier transform) by the process executing unit 206 or another imaging processor. Each A-scan data is a spectral intensity distribution.

The processing performed by the map creating unit 202 may include processing on the basis of the technique disclosed in the above-mentioned Japanese Patent No. 6,230,023 (US Patent Application Publication No. 2014/0293289). In brief, the technique includes the following steps: a step of applying a high pass filter to A-scan data representing a spectral intensity distribution corresponding to a specific XY position, to extract its amplitude component; and a step of determining a single estimated intensity value (representative intensity value) from the extracted amplitude component based on the inverse cumulative distribution function (inverse CDF).

Figure 5:
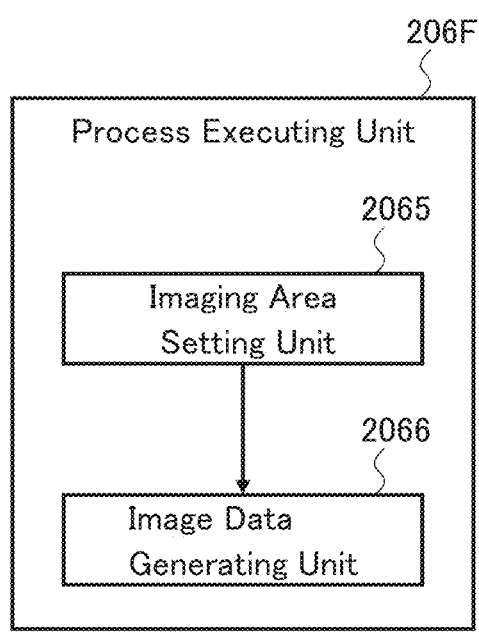
FIG. 5 is a schematic diagram illustrating the configuration of the ophthalmic apparatus according to the exemplary aspect.

More specifically, as described in FIG. 5 and its description of Japanese Patent No. 6,230,023 (US Patent Application Publication No. 2014/0293289), the map creating unit 202 in some exemplary aspects may be configured to execute the following steps: a step of applying high pass filtering to A-scan data; a step of applying down-sampling to the filtered A-scan data (or a step of truncating the filtered A-scan data); a step of squaring the down-sampled A-scan data (or a step of taking an absolute value of the down-sampled A-scan data); a step of sorting the results of the squaring (or a step of selecting a quantile); a step of performing calculation using the inverse CDF method; and a step of determining a single estimated intensity value (representative intensity value) from the result of the calculation.

In some other exemplary aspects, the map creating unit 202 may be configured to execute the following steps: a step of applying high pass filtering to A-scan data; a step of applying down-sampling to the filtered A-scan data (or a step of truncating the filtered A-scan data); a step of squaring the down-sampled A-scan data (or a step of taking an absolute value of the down-sampled A-scan data); a step of selecting the largest percentile value in the result of the squaring; and a step of determining a single estimated intensity value (representative intensity value) from the largest percentile value selected.

In still some other exemplary aspects, the map creating unit 202 may be configured to perform the following steps: a step of applying high pass filtering to A-scan data; a step of applying down-sampling to the filtered A-scan data (or a step of truncating the filtered A-scan data); a step of selecting the smallest and largest percentile values from the down-sampled A-scan data; a step of squaring each of the smallest and largest percentile values selected (or a step of taking an absolute value of each of the smallest and largest percentile values selected); and a step of combining the squared smallest percentile value and the squared largest percentile value (e.g., calculating their average, or selecting a percentile value using the inverse CDF method).

For details of the map creating technique exemplified above, Japanese Patent No. 6,230,023 (US Patent Application Publication No. 2014/0293289) may be referred to. Further, applicable map creating techniques are not limited to the above-described examples, and any technique within the scope of the disclosure in Japanese Patent No. 6,230,023 (US Patent Application Publication No. 2014/0293289) or any modification thereof may be applied.

Representative intensity values corresponding to a plurality of XY positions may be obtained by applying the above-described series of steps to each A-scan data in the three dimensional data set. Then, a two dimensional map representing the distribution of the representative intensity values in the XY plane may be created by mapping the correspondence relationships between the XY positions and the representative intensity values.

The two dimensional map created by the map creating unit 202 is input to the placing unit 204. The placing unit 204 performs the placement of the three dimensional data set based on the two dimensional map.

For example, the placing unit 204 determines the correspondence (the positional relationship) between the three dimensional data set and a region of the sample by analyzing the two dimensional map and detecting an image of a predetermined site of the eye 120. Alternatively, the placing unit 204 analyzes the two dimensional map based on the three dimensional data set to detect an image of a predetermined site, analyzes another two dimensional map based on another three dimensional data set to detect another image of the predetermined site, and then determines the correspondence (the positional relationship) between the two three dimensional data sets based on the two images detected. Alternatively, the placing unit 204 analyzes the two dimensional map based on the three dimensional data set to detect an image of a predetermined site, analyzes another two dimensional map based on another three dimensional data set to detect an image of another predetermined site, and then determines the correspondence (the positional relationship) between the two three dimensional data sets based on the two images detected. Alternatively, the placing unit 204 analyzes the two dimensional map based on the three dimensional data set to detect an image of a predetermined site, and determines the correspondence (the positional relationship) between the three dimensional data set and examination data by associating the detected image and a specific part of the examination data.

The predetermined site for image detection may be, for example, any of the followings: lesion; blood vessel; optic nerve head; macula; sub-tissue of eye fundus (e.g., inner limiting membrane, nerve fiber layer, ganglion cell layer, inner plexiform layer, inner nuclear layer, outer plexiform layer, outer nuclear layer, external limiting membrane, photoreceptor layer, retinal pigment epithelium layer, Bruch membrane, choroid, sclera, etc.); sub-tissue of cornea (e.g., corneal epithelium, Bowman's membrane, corneal stroma, Dua's layer, Descemet's membrane, corneal endothelium, etc.); iris; crystalline lens; Zinn's zonule; ciliary body; vitreous body; and other ocular tissues.

Any image processing technique may be applied to the detection of the image of the predetermined site described above. For example, the image detection may be executed using any image classification technique, any image detection technique, any image recognition technique, any image segmentation technique, any deep learning technique, and/or other techniques. As an example, the placing unit 204 may analyze the two dimensional map created from the three dimensional data set acquired by applying OCT scanning to the fundus to detect an image of the optic nerve head. Then, the placing unit 204 may perform the placement of the three dimensional data set based on the optic nerve head image detected from the two dimensional map.

In another example, the controlling device 126 displays the two dimensional map on the display device (not shown in the drawings). The user designates a desired region in the two dimensional map displayed, using an operation device (not shown in the drawings). The placing unit 204 may perform the placement of the three dimensional data set based on the region designated by the user in the displayed two dimensional map.

Data usable for the three dimensional data set placement is not limited to such a two dimensional map. For example, any of the following data may be referred to for the placement of the three dimensional data set: data generated from a two dimensional map; data used in a process prior to the creation of a two dimensional map; and data generated from data used in a process prior to the creation of a two dimensional map. Here, the data used in a process prior to the two dimensional map creation may be a three dimensional region or a three dimensional data set.

The three dimensional data set on which the placement has been performed by the placing unit 204 is input to the process executing unit 206. The process executing unit 206 executes processing based on the partial data set of the placed three dimensional data set.

Hereinafter, examples of various kinds of processes executable by the process executing unit 206 will be described. Specifically, some examples of analysis, evaluation, setting of a region of interest (ROI), setting of an examination area, setting of an imaging area, and a comparison with examination data will be described. Here, the region of interest may be an analysis target region (region to be analyzed), an evaluation target region (region to be evaluated). Note that, any two or more of such examples may be combined. The process executing unit 206 includes some elements shown in two or more examples combined. For example, the process executing unit 206 may include one, some or all of the elements shown in FIGS. 3A to 6.

Figure 3A:
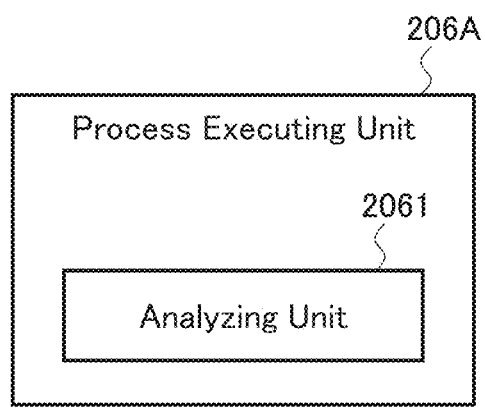
FIG. 3A is a schematic diagram illustrating the configuration of the ophthalmic apparatus according to the exemplary aspect.

The process executing unit 206A shown in FIG. 3A includes the analyzing unit 2061 configured to execute one or more predetermined analysis processes based on a partial data set of the three dimensional data set.

For example, the analyzing unit 2061 performs layer thickness analysis. The site on which the layer thickness analysis is performed may be any ocular tissue such as the followings: the retina; a sub-tissue of the retina; a combination of two or more sub-tissues of the retina; the choroid; a sub-tissue of the choroid; a combination of two or more sub-tissues of the choroid; the cornea; a sub-tissue of the cornea; a combination of two or more sub-tissues of the cornea; and the crystalline lens. The layer thickness analysis includes, for example, segmentation and thickness measurement. The segmentation is a process of identifying a region (a partial data set) of the three dimensional data set corresponding to such a target site. The thickness measurement is a process of measuring the thickness of the identified partial data set at one or more measurement positions. Further, the analyzing unit 2061 may be configured to determine the positions in the eye 120 corresponding to respective layer thickness measurement positions based on the result of the placement process executed by the placing unit 204. This makes it possible to grasp on which position or site in the eye 120 the layer thickness measurement has actually been performed.

The analysis process executable by the analyzing unit 2061 is not limited to the layer thickness analysis. Another example is size analysis to measure the size of a tissue. The tissue to be measured by the size analysis may be the optic nerve head, a lesion, or a blood vessel. Examples of parameters of the optic nerve head to be measured may include cup diameter, disk diameter, rim diameter, and depth. Examples of parameters of a lesion to be measured may include area, volume, and length. Examples of parameters of a blood vessel to be measured may include thickness (width, diameter) and length. The size analysis includes, for example, segmentation and measurement. Here, the segmentation is a process of identifying a region (a partial data set) of the three dimensional data set corresponding to such a target tissue, and the measurement is a process of measuring a specific size of the partial data set identified. The analyzing unit 2061 may be configured to determine the position in the eye 120 corresponding to the size measurement position (target tissue) based on the result of the placement process executed by the placing unit 204. This makes it possible to grasp at which position or site of the eye 120 the size has been measured.

Another example of the analysis process is shape analysis for measuring the shape of a tissue. The tissue to be subjected to the shape analysis may be the optic nerve head, a lesion, a blood vessel, or other tissues. The shape analysis includes, for example, segmentation and shape determination. Here, the segmentation is a process of identifying a region (a partial data set) of the three dimensional data set corresponding to such a target tissue, and the shape determination is a process of determining the shape of the partial data set identified. The shape determination includes, for example, a process of extracting the contour of the partial data set, and a process of calculating a shape parameter of the contour (e.g., circularity, roundness, ellipticity, cylindricity). Further, the analyzing unit 2061 may be configured to determine the position in the eye 120 corresponding to the shape measurement position (target tissue) based on the result of the placement process executed by the placing unit 204. This makes it possible to grasp at which position or site of the eye 120 the shape has been measured.

In addition to the shape measurement as described above, orientation analysis may be performed. The orientation analysis is a process of measuring the orientation of the target tissue. The orientation analysis includes, for example, a process of determining a geometric shape (figure) that approximates the contour shape of the partial data set, and a process of determining the orientation of the approximate figure. For example, the figure is an approximate ellipse, and the orientation of the approximate ellipse is the orientation of its major axis. In another example, the orientation analysis includes a process of determining a specific parameter of the partial data set, and a process of determining the orientation based on the parameter. For example, the parameter is the maximum diameter, and the orientation based on the maximum diameter is the orientation of the line segment along the maximum diameter.

Figure 3B:
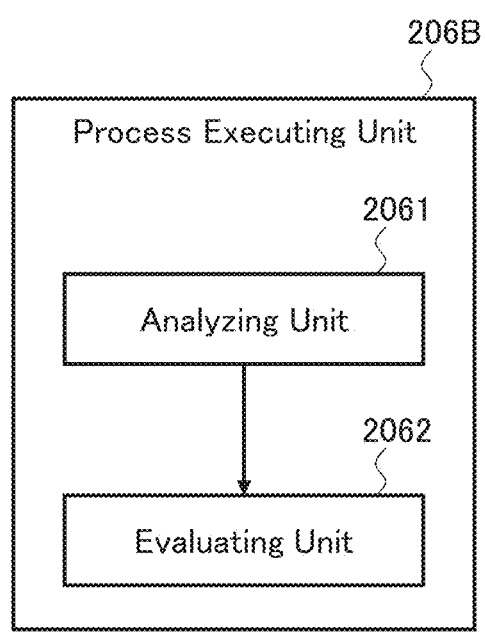
FIG. 3B is a schematic diagram illustrating the configuration of the ophthalmic apparatus according to the exemplary aspect.

The process executing unit 206B shown in FIG. 3B includes the analyzing unit 2061 and the evaluating unit 2062. The analyzing unit 2061 is configured to execute an analysis process based on a partial data set of the three dimensional data set. The evaluating unit 2062 is configured to execute an evaluation process based on data obtained by the analysis process. The analyzing unit 2061 may be the same as the analyzing unit 2061 in FIG. 3A.

For example, the evaluating unit 2062 compares the data obtained by the analyzing unit 2061 with normative data. By so doing, the evaluating unit 2062 can evaluate whether or not the data of the eye 120 is normal (i.e., whether or not there is a suspected disease), determine the degree or stage of disease, or determine the degree of suspicion of disease.

The evaluation process executed by the evaluating unit 2062 is not limited to the comparison with normative data, and may include any evaluation processing using statistics, any evaluation processing using computations or operations, or the like.

Figure 3C:
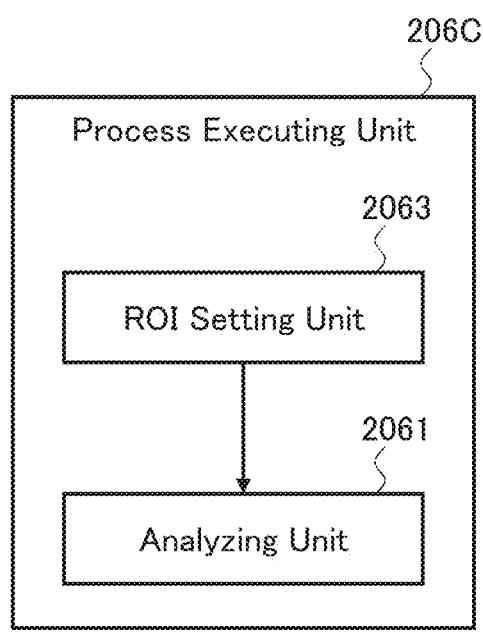
FIG. 3C is a schematic diagram illustrating the configuration of the ophthalmic apparatus according to the exemplary aspect.

The process executing unit 206C shown in FIG. 3C includes the region of interest (ROI) setting unit 2063 and the analyzing unit 2061. The ROI setting unit 2063 is configured to set a partial data set to which the analysis process is applied. The partial data set is a region of interest that is at least part of the three dimensional data set. The analyzing unit 2061 is configured to execute a predetermined analysis process based on the partial data set. The analyzing unit 2061 may be the same as the analyzing unit 2061 in FIG. 3A.

The ROI setting unit 2063 sets a region of interest by analyzing the three dimensional data set, for example. The setting of the region of interest includes, for example, segmentation for identifying a region of interest in the three dimensional data set.

In another example, the controlling device 126 displays a two dimensional map (or an image generated based on a three dimensional data set) on a display device (not shown in the drawings). The user designates a desired region in the displayed two dimensional map (or the displayed image) using an operation device (not shown in the drawings). The ROI setting unit 2063 may set the region of interest in the three dimensional data set based on the region in the displayed two dimensional map (or the displayed image) designated by the user.

The region of the eye corresponding to the region of interest may include, for example, any of the followings: lesion; blood vessel; optic nerve head; macula; sub-tissue of eye fundus (e.g., inner limiting membrane, nerve fiber layer, ganglion cell layer, inner plexiform layer, inner nuclear layer, outer plexiform layer, outer nuclear layer, external limiting membrane, photoreceptor layer, retinal pigment epithelium layer, Bruch membrane, choroid, sclera, etc.); sub-tissue of cornea (e.g., corneal epithelium, Bowman's membrane, corneal stroma, Dua's layer, Descemet's membrane, corneal endothelium, etc.); iris; crystalline lens; Zinn's zonule; ciliary body; vitreous body; and other ocular tissues.

The evaluating unit 2062 may be combined with the process executing unit 206C shown in FIG. 3C. The evaluating unit 2062 of the present example executes a predetermined evaluation process, based on the data obtained by the analysis process executed by the analyzing unit 2061 on the basis of the partial data set defined by the ROI setting unit 2063. The evaluating unit 2062 of the present example may be the same as the evaluating unit 2062 in FIG. 3B.

Figure 3D:
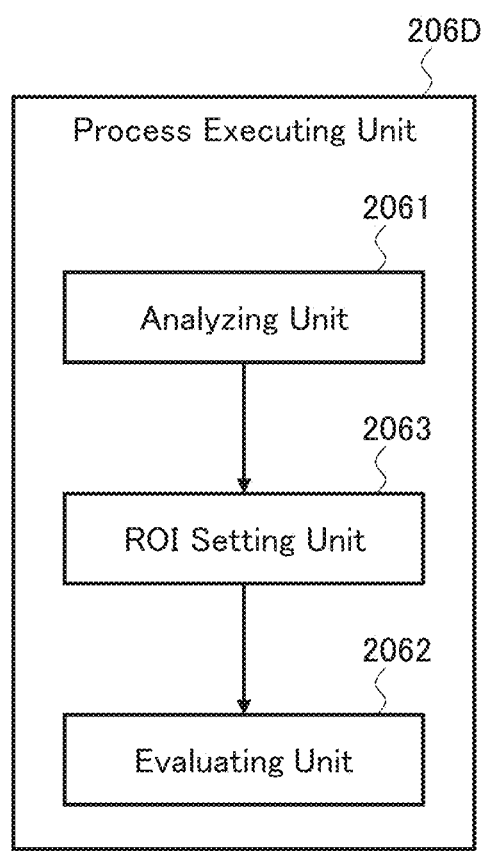
FIG. 3D is a schematic diagram illustrating the configuration of the ophthalmic apparatus according to the exemplary aspect.

The process executing unit 206D shown in FIG. 3D includes the analyzing unit 2061, the ROI setting unit 2063, and the evaluating unit 2062. The analyzing unit 2061 is configured to perform a predetermined analysis process based on a partial data set of a three dimensional data set. The ROI setting unit 2063 is configured to set partial data of the data acquired by the analysis process, to which an evaluation process is to be applied. The partial data is a region of interest that is at least part of the analysis data. The evaluating unit 2062 is configured to perform a predetermined evaluation process based on the region of interest set by the ROI setting unit 2063. The analyzing unit 2061 may be the same as the analyzing unit 2061 in FIG. 3A. The evaluating unit 2062 may be the same as the evaluating unit 2062 in FIG. 3B.

The ROI setting unit 2063, for example, identifies a partial data set by analyzing a three dimensional data set, and then sets, as a region of interest, partial data of analysis data corresponding to the partial data set. The setting of the partial data set includes segmentation, for example.

In another example, the ROI setting unit 2063 sets a region of interest by analyzing analysis data obtained by the analyzing unit 2061. As an example, the ROI setting unit 2063 performs a process of detecting characteristic partial data from the analysis data, and a process of setting a region of interest based on the partial data detected.

In yet another example, the controlling device 126 displays a two dimensional map (or, an image generated based on a three dimensional data set, or analysis data) on a display device (not shown in the drawings). The user designates a desired region in the displayed two dimensional map (or, the displayed image or the displayed analysis data) using an operation device (not shown in the drawings). The ROI setting unit 2063 may set a region of interest in the analysis data based on the region designated by the user in the displayed two dimensional map (or, the displayed image or the displayed analysis data).

Figure 4:
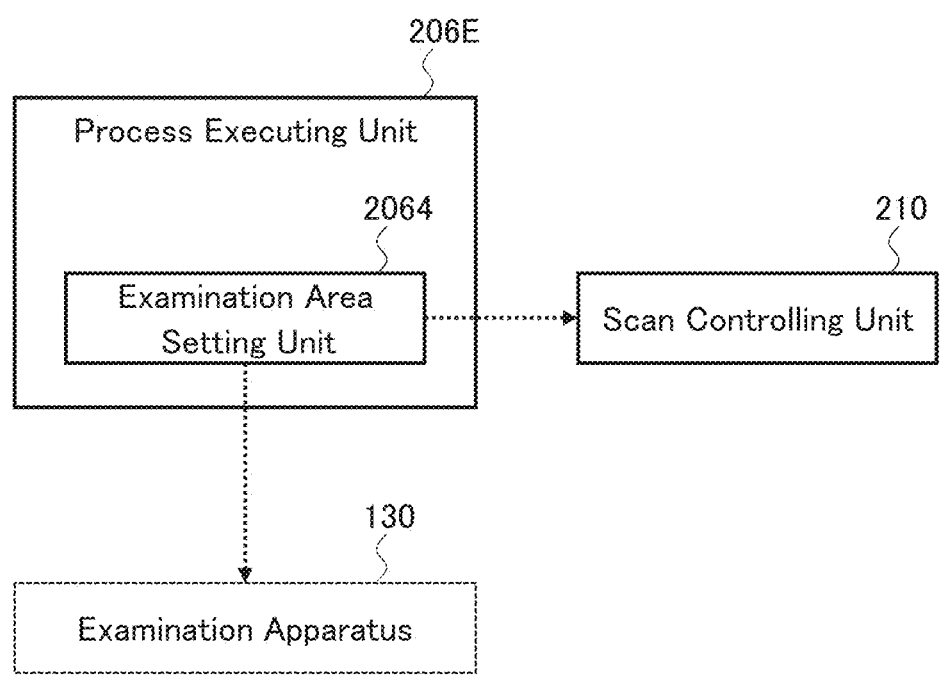
FIG. 4 is a schematic diagram illustrating the configuration of the ophthalmic apparatus according to the exemplary aspect.

The process executing unit 206E shown in FIG. 4 includes the examination area setting unit 2064. The examination area setting unit 2064 is configured to execute the setting of an area to which a predetermined examination is applied for the eye 120. The area is referred to as an examination area. The predetermined examination may be of any kind, and may be OCT scanning, visual field examination (perimetry), microperimetry, electrophysiological examination, or other (ophthalmic) examinations.

For example, the examination area setting unit 2064 performs the following processes: a process of determining a site that requires attention (a site requiring attention) of the eye 120 by analyzing any one or more of a two dimensional map, a three dimensional data set, and data generated based on at least one of the two dimensional map and the three dimensional data set; and a process of setting an examination area based on the site requiring attention determined. The site requiring attention is, for example, a lesion, a specific site, a specific tissue, or the like. Typically, the examination area is set to include at least part of the site requiring attention.

In one example, the examination area setting unit 2064 performs the following processes: segmentation on a two dimensional map (or, on a three dimensional data set); a process of converting the region in the two dimensional map identified by the segmentation into a site requiring attention in the eye 120 based on the result of the placement process described above; and a process of setting an examination area based on the site requiring attention.

In the event that an examination area set by the examination area setting unit 2064 is an area to which OCT scanning is applied, information indicating the examination area may be provided to the scan controlling unit 210. The scan controlling unit 210 controls the OCT scanner 220 to apply an OCT scan to the examination area indicated by the provided information.

In the event that the examination area set by the examination area setting unit 2064 is an area to which OCT scanning is applied, information indicating the examination area may be provided to another OCT apparatus (e.g., the examination apparatus 130) using the communication device described above.

In the event that the examination area set by the examination area setting unit 2064 is an area to which a certain examination is applied, information indicating the examination area may be provided to the examination apparatus 130 corresponding to the concerned examination via the communication device described above.

The process executing unit 206F shown in FIG. 5 includes the imaging area setting unit 2065 and the image data generating unit 2066. The imaging area setting unit 2065 is configured to set a partial data set to which the imaging process is applied. Here, the partial data set is an imaging area (area to be imaged) that is at least part of the three dimensional data set. The image data generating unit 2066 is configured to generate image data of the imaging area set by the imaging area setting unit 2065.

The imaging process includes at least Fourier transform. Examples of the imaging process include general OCT image construction, motion contrast (e.g., OCT angiography), phase image construction, polarization image construction, and other image constructions.

For example, the imagining area setting unit 2065 performs the following processes: a process of determining a site requiring attention of the eye 120 by analyzing any one or more of a two dimensional map, a three dimensional data set, and data generated based on at least one of the two dimensional map and the three dimensional data set; and a process of setting an imaging area based on the site requiring attention determined. The site requiring attention is, for example, a lesion, a specific site, a specific tissue, or the like. Typically, the imaging area is set to include at least part of the site requiring attention.

In one example, the imaging area setting unit 2065 performs the following processes: segmentation on a two dimensional map (or a three dimensional data set); a process of converting the region in the two dimensional map identified by the segmentation into a site requiring attention in the eye 120 based on the result of the placement process described above; and a process of setting an imaging area based on the site requiring attention.

The image data generating unit 2066 is configured to generate image data based on data acquired by the OCT scanner 220. For example, the image data generating unit 2066 constructs image data of a cross sectional image of the eye 120 based on an output from the OCT scanner 220. The output is referred to as sampled data or interference signal data. Such image data generating processing includes filtering, fast Fourier transform (FFT) etc. as in conventional OCT techniques (e.g., swept source or spectral domain OCT technique). With such processing, reflection intensity profiles are acquired for the A-lines respectively corresponding to the XY positions, and a group of image data for the A-lines is constructed by performing the imaging process on the reflection intensity profiles. Here, each A-line is a scan path of the measurement light beam in the eye 120, and each reflection intensity profile lies along the Z direction. Further, image data for an A-line is referred to as A-scan image data.

Furthermore, the image data generating unit 2066 may be configured to construct two dimensional image data or three dimensional image data, by constructing a plurality of pieces of A-scan image data according to the OCT scan mode and then arranging the plurality of pieces of A-scan image data. The OCT scan mode is concerned with, for example, measurement light beam deflection and A-scan position transition.

In the case where a plurality of pieces of cross sectional image data is obtained by raster scan or another scan mode, the image data generating unit 2066 may construct stack data by embedding the plurality of pieces of cross sectional image data in a single three dimensional coordinate system. In addition, the image data generating unit 2066 may construct voxel data (volume data) by applying voxelization to the stack data.

The image data generating unit 2066 may be configured to perform rendering on the stack data or the volume data. A rendering technique applied thereto is optional. For example, any of volume rendering, multi planar reconstruction (MPR), surface rendering, and other rendering techniques may be applied thereto. Furthermore, the image data generating unit 2066 may be configured to construct a planar image from the stack data or the volume data. Examples of the planar image include a front image and en-face image. For example, the image data generating unit 2066 may be configured to construct a projection image by integrating the stack data or the volume data along their A-lines.

In the present example, the image data generating unit 2066 generates image data by applying the imaging process to an OCT data set included in the imaging area defined by the imaging area setting unit 2065. The OCT data set included in the imaging area is a partial data set of the three dimensional data set.

In another example, the image data generating unit 2066 generates image data by applying the imaging process to the three dimensional data set. Further, the process executing unit 206F extracts, from the image data, partial image data corresponding to the imaging area defined by the imaging area setting unit 2065. The partial image data extraction may include processing such as clipping, cropping or trimming.

The process executing unit 206F shown in FIG. 5 has the image constructing function (the image data generating unit 2066); however, OCT apparatuses (ophthalmic apparatuses) of other exemplary aspects may not have the image constructing function. In such cases, information indicating the imaging area set by the imaging area setting unit 2065 may be provided to an external device (including an imaging processor) via a communication device (not shown in the drawings).

Figure 6:
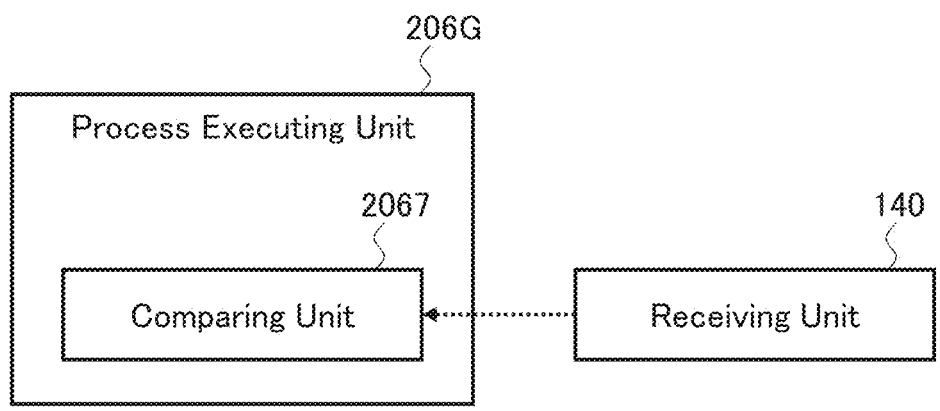
FIG. 6 is a schematic diagram illustrating the configuration of the ophthalmic apparatus according to the exemplary aspect.

The example shown in FIG. 6 is provided with the receiving unit 140 configured to receive data acquired from the eye 120 by a predetermined examination different from OCT. The data acquired by the examination is referred to as examination data. Further, the process executing unit 206G of the present example includes the comparing unit 2067. The comparing unit 2067 is configured to execute a predetermined comparison process that compares at least part of the examination data received by the receiving unit 140 with at least part of the three dimensional data set acquired by the OCT scanner 220.

The receiving unit 140 receives examination data obtained from the eye 120, from the outside (e.g., an ophthalmic apparatus, an image archiving system, a recording medium). The receiving unit 140 may include a communication device or a drive device, for example.

Examination data may be obtained by any kind of modality or any kind of examination. Examples of examination data include sensitivity distribution data obtained by visual field examination of the eye 120, electroretinogram (ERG) obtained by electrophysiological examination, tear film distribution data obtained by tear film photography (anterior eye segment photography), etc.

The comparing unit 2067 may be configured to perform the following processes, for example: registration between the examination data and a two dimensional map based on the result of the placement process performed by the placing unit 204; registration between the examination data and a three dimensional data set based on the result of the prior registration; and a predetermined comparison process based on the examination data and (at least part of) the three dimensional data set to which the registration has been performed.

The comparison process may include any one or more of the following examples: a comparison between a three dimensional data set and examination data; a comparison between a two dimensional map based on a three dimensional data set and examination data; a comparison between image data based on a three dimensional data set and examination data; a comparison between analysis data of a two dimension map and examination data; a comparison between analysis data of image data and examination data; a comparison between a three dimensional data set and processed data of examination data; a comparison between a two dimensional map based on a three dimensional data set and processed data of examination data; a comparison between image data based on a three dimensional data set and processed data of examination data; a comparison between analysis data of a two dimensional map and processed data of examination data; and a comparison between analysis data of image data and processed data of examination data.

The processing device 124 may be capable of performing various kinds of data processing other than the data processing examples described above. The processing device 124 may be configured to process data acquired by OCT scanning (OCT data). The OCT data is, for example, interference signal data, reflection intensity profiles, or image data. Note that interference signal data is at least part of three dimensional data set.

The processing device 124 may be capable of processing data other than OCT data. For example, in the event that the ophthalmic apparatus 100 includes a data acquisition device other than the OCT scanner 220, the processing device 124 may be configured to process data acquired by the data acquisition device. An ophthalmic apparatus adoptable to the data acquisition device may be any ophthalmic imaging apparatus such as a fundus camera, scanning laser ophthalmoscope (SLO), surgical microscope, or slit lamp microscope. An ophthalmic apparatus adoptable to the data acquisition device may be any ophthalmic measurement apparatus such as a refractometer, keratometer, tonometer, eye axial length measurement device, specular microscope, wave front analyzer, or perimeter. Further, in the event that the OCT apparatus is a medical apparatus of any kind, that is, in the event that the OCT apparatus is an apparatus used in any medical department, the medical apparatus adopted as the data acquisition device may be a medical imaging apparatus of any kind and/or medical examination apparatus of any kind. In addition, an OCT apparatus used in any field other than medical care includes a data acquisition device corresponding to the application field.

Described below are several examples of operations executable by the ophthalmic apparatus 100 having the configuration examples described above.

Figure 7:
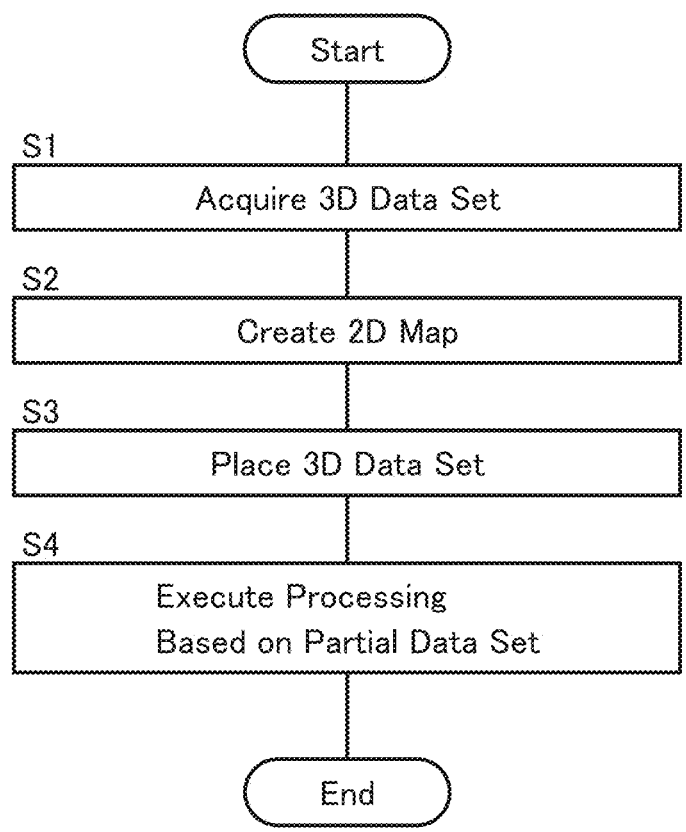
FIG. 7 is a flowchart illustrating the operation of the ophthalmic apparatus according to the exemplary aspect.

Moving now on to FIG. 7. The present operation example begins with that the scan controlling unit 210 controls the OCT scanner 220 to acquire a three dimensional data set by applying an OCT scan to the eye 120 (S1).

Next, the map creating unit 202 creates a two dimensional map based on representative intensity values respectively of a plurality of pieces of A-scan data included in the three dimensional data set acquired in step S1 (S2).

Next, the placing unit 204 places the three dimensional data set acquired in step S1, based on the two dimensional map created in step S2 (S3).

Next, the process executing unit 206 executes processing based on a partial data set of the three dimensional data set on which the placement has been performed in step S3 (S4).

The process executed in step S4 may include any one or more of the followings, for example: analysis; evaluation; setting of a region of interest; setting of an examination area; setting of imaging area; image data generation; and comparison with examination data. In other words, the process executing unit 206 may include any one or more of the analyzing unit 2061, the evaluating unit 2062, the ROI setting unit 2063, the examination area setting unit 2064, the imaging area setting unit 2065, the image data generating unit 2066, and the comparing unit 2067.

As an example, in the event that the process of step S4 includes setting of an area to which OCT scanning is applied, which is an example of examination area setting, information indicating the examination area set in step S4 is provided to the scan controlling unit 210. The scan controlling unit 210 controls the OCT scanner 220 to acquire a data set by applying an OCT scan targeting the examination area set in step S4. The process executing unit 206 (the image data generating unit 2066 therein) generates image data from the data set acquired. The controlling device 126 may display the generated image data on a display device (not shown in the drawings). The display device may be any of, for example, an element of the ophthalmic apparatus 100, a peripheral device of the ophthalmic apparatus 100, and an apparatus (such as a remote medical apparatus) connectable to the ophthalmic apparatus 100 via a communication line. Further, the controlling device 126 can store the generated image data in a storage device (not shown in the drawings). The storage device may be any of, for example, an element of the ophthalmic apparatus 100, a peripheral device of the ophthalmic apparatus 100, an apparatus connectable to the ophthalmic apparatus 100 via a communication line, and a portable recording medium.

Some effects of the ophthalmic apparatus (OCT apparatus) 100 of the present aspect will be described.

The ophthalmic apparatus 100 according to the present aspect includes the OCT scanner 220, the map creating unit 202, the placing unit 204, and the process executing unit 206. The OCT scanner 220 is configured to acquire a three dimensional data set by applying an OCT scan to the sample (the eye 120). The map creating unit 202 is configured to create a two dimensional map based on representative intensity values of a plurality of pieces of A-scan data included in the three dimensional data set. The placing unit 204 is configured to place the three dimensional data set based on the two dimensional map. The process executing unit 206 is configured to execute a process based on at least a partial data set of the three dimensional data set on which placement based on the two dimensional map has been performed.

According to the ophthalmic apparatus 100 configured in this way, the placement of the three dimensional data set may be executed based on the two dimensional map created from the three dimensional data set acquired by the OCT scan, and then processing may be executed based on the three dimensional data set on which the placement has already been performed. Therefore, processing relating to a desired region of the sample can be performed without having to perform the three dimensional image construction and/or the landmark detection (landmark identification) as in the invention described in U.S. Pat. No. 7,884,945 and U.S. Pat. No. 8,405,834. This makes it possible to improve effective utilization of resources required for processing and shorten processing time, thereby achieving further efficiency improvement in OCT data processing. Consequently, real-time processing can be preferably performed, for example.

In the ophthalmic apparatus 100 of the present aspect, the process executing unit 206 may include the analyzing unit 2061 that is configured to perform a predetermined analysis process based on at least a partial data set of the three dimensional data set on which the placement has been performed.

According to such a configuration, analysis on a desired region of the sample can be performed without having to perform the three dimensional image construction and/or the landmark detection (landmark identification) as in the conventional technology. This makes it possible to improve effective utilization of resources required for analysis and shorten processing time, thereby achieving further efficiency improvement in analysis. Consequently, real-time analysis can be preferably performed, for example.

In the ophthalmic apparatus 100 of the present aspect, the process executing unit 206 may include the evaluating unit 2062 that is configured to perform a predetermined evaluation process based on the analysis data obtained by the analyzing unit 2061.

According to such a configuration, an evaluation on a desired region of the sample can be performed without having to perform the three dimensional image construction and/or the landmark detection (landmark identification) as in the conventional technology. This makes it possible to improve effective utilization of resources required for evaluation and shorten processing time, thereby achieving further efficiency improvement in evaluation. Consequently, real-time evaluation can be preferably performed, for example.

In the ophthalmic apparatus 100 of the present aspect, the process executing unit 206 may include the ROI setting unit 2063 that is configured to set a region of interest (ROI) such as an analysis target region and/or evaluation target region.

According to such a configuration, a region of interest can be set without having to perform the three dimensional image construction and/or the landmark detection (landmark identification) as in the conventional technology. This makes it possible to improve effective utilization of resources required for ROI setting and shorten processing time, thereby achieving further efficiency improvement in ROI setting. Consequently, a region of interest can be preferably set in real-time, for example.

In the ophthalmic apparatus 100 of the present aspect, the process executing unit 206 may include the examination area setting unit 2064 that is configured to set a predetermined area to which examination is applied for the sample (examination area for the sample).

According to such a configuration, an examination area can be set without having to perform the three dimensional image construction and/or the landmark detection (landmark identification) as in the conventional technology. This makes it possible to improve effective utilization of resources required for examination area setting and shorten processing time, thereby achieving further efficiency improvement in examination area setting. Consequently, an examination area can be preferably set in real-time, for example.

In the ophthalmic apparatus 100 of the present aspect, the process executing unit 206 may include the imaging area setting unit 2065 that is configured to set a partial data set (an imaging area) to which a predetermined imaging process is applied.

According to such a configuration, an imaging area can be set without having to perform the three dimensional image construction and/or the landmark detection (landmark identification) as in the conventional technology. This makes it possible to improve effective utilization of resources required for imaging area setting and shorten processing time, thereby achieving further efficiency improvement in imaging area setting. Consequently, an imaging area can be preferably set in real-time, for example.

The ophthalmic apparatus 100 of the present aspect may include a device for preparing examination data acquired from the sample by a predetermined examination different from OCT. The examination data preparing device includes, for example, a device for receiving examination data (the receiving unit 140) or a device for acquiring examination data by applying examination to the sample. Furthermore, the process executing unit 206 may include the comparing unit 2067 that is configured to execute a predetermined comparison process of comparing the examination data with at least part of the three dimensional data set.

According to such a configuration, a comparison process between the examination data and the OCT data can be executed without having to perform the three dimensional image construction and/or the landmark detection (landmark identification) as in the conventional technology. This makes it possible to improve effective utilization of resources required for a comparison process and shorten processing time, thereby achieving further efficiency improvement in a comparison process. Consequently, a comparison process can be preferably performed in real-time, for example.

The sample in the present aspect is a living eye as described above; however, samples in some other aspects may be objects other than living eyes and OCT apparatuses may have the same and/or like functions and configurations. In other words, any of the matters (e.g., functions, hardware configurations, software configurations, etc.) regarding the ophthalmic apparatus 100 may be combined with an OCT apparatus of any aspect. The matters combined yield or provide actions and effects accordingly.

Some exemplary aspects relate to a method of controlling an OCT apparatus including a processor and an OCT scanner that applies an OCT scan to a sample. The control method may include at least the following steps: a step of controlling the OCT scanner to acquire a three dimensional data set from a sample; a step of controlling the processor to create a two dimensional map based on representative intensity values of a plurality of pieces of A-scan data included in the three dimensional data set; a step of controlling the processor to perform placement of the three dimensional data set based on the two dimensional map; and a step of controlling the processor to execute a process based on at least a partial data set of the three dimensional data set on which the placement has been performed.

Any of the matters (e.g., functions, hardware configurations, software configurations, etc.) regarding the ophthalmic apparatus 100 may be combined with the control method of the present aspect. The matters combined yield or provide actions and effects accordingly.

Some exemplary aspects relate to a program that causes a computer to execute such a control method of an OCT apparatus. Any of the matters described regarding the ophthalmic apparatus 100 may be combined with such a program. Further, some exemplary aspects relate to a computer-readable non-transitory recording medium storing such a program. Any of the matters described regarding the ophthalmic apparatus 100 may be combined with such a recording medium.

Some exemplary aspects relate to an apparatus for processing data acquired using OCT (an OCT data processing apparatus). The OCT data processing apparatus may include at least the following elements: a receiving unit that receives a three dimensional data set acquired by applying an OCT scan to a sample; a map creating unit that creates a two dimensional map based on representative intensity values of a plurality of pieces of A-scan data included in the three dimensional data set; a placing unit that performs placement of the three dimensional data set based on the two dimensional map; and a process executing unit that executes a process based on at least a partial data set of the three dimensional data set on which the placement has been performed.

In other words, the OCT data processing apparatus is an apparatus that includes an element (a receiving unit) that receives a three dimensional data set acquired by an OCT scan from the outside (e.g., an OCT apparatus, an image archiving system, a recording medium), in place of or in addition to the OCT scanner 220 of the OCT apparatus (the ophthalmic apparatus) 100 described above. The receiving unit may include a communication device or a drive device, for example.

Any of the matters (e.g., functions, hardware configurations, software configurations, etc.) regarding the ophthalmic apparatus 100 may be combined with the OCT data processing apparatus of the present aspect. The matters combined yield or provide actions and effects accordingly.

Some exemplary aspects relate to a method of controlling an OCT data processing apparatus including a processor. The control method may include at least the following steps: a step of controlling the processor to receive a three dimensional data set acquired by applying an OCT scan to a sample; a step of controlling the processor to create a two dimensional map based on representative intensity values of a plurality of pieces of A-scan data included in the three dimensional data set; a step of controlling the processor to perform placement of the three dimensional data set based on the two dimensional map; and a step of controlling the processor to execute a process based on at least a partial data set of the three dimensional data set on which the placement has been performed.

Any of the matters (e.g., functions, hardware configurations, software configurations, etc.) regarding the ophthalmic apparatus 100 may be combined with the control method of the present aspect. The matters combined yield or provide actions and effects accordingly.

Some exemplary aspects relate to a program that causes a computer to execute such a control method of the OCT data processing apparatus. Any of the matters described regarding the ophthalmic apparatus 100 may be combined with the program. Further, some exemplary aspects relate to a computer-readable non-transitory recording medium storing such a program. Any of the matters described regarding the ophthalmic apparatus 100 may be combined with the recording medium.

A method of processing OCT data may be provided by an OCT apparatus (e.g., the ophthalmic apparatus 100) of some exemplary aspects, a control method of an OCT apparatus of some exemplary aspects, an OCT data processing apparatus of some exemplary aspects, or a control method of an OCT data processing apparatus of some exemplary aspects. Such an OCT data processing method thus provided may include at least the following steps: a step of preparing a three dimensional data set acquired from a sample; a step of creating a two dimensional map based on representative intensity values of a plurality of pieces of A-scan data included in the three dimensional data set; a step of placing the three dimensional data set based on the two dimensional map; and a step of executing a process based on at least a partial data set of the three dimensional data set on which placement has been performed.

Any of the matters (e.g., functions, hardware configurations, software configurations, etc.) regarding the ophthalmic apparatus 100 may be combined with the OCT data processing method of the present aspect. The matters combined yield or provide actions and effects accordingly.

Some exemplary aspects relate to a program that causes a computer to execute such an OCT data processing method. Any of the matters described regarding the ophthalmic apparatus 100 may be combined with the program. Further, some exemplary aspects relate to a computer-readable non-transitory recording medium storing such a program. Any of the matters described regarding the ophthalmic apparatus 100 may be combined with the recording medium.

In some aspects, the non-transitory recording medium on which the program is stored may be in any form, and examples thereof include a magnetic disk, an optical disk, a magneto-optical disk, a semiconductor memory, and the like.

Second Aspect Example

Figure 8:
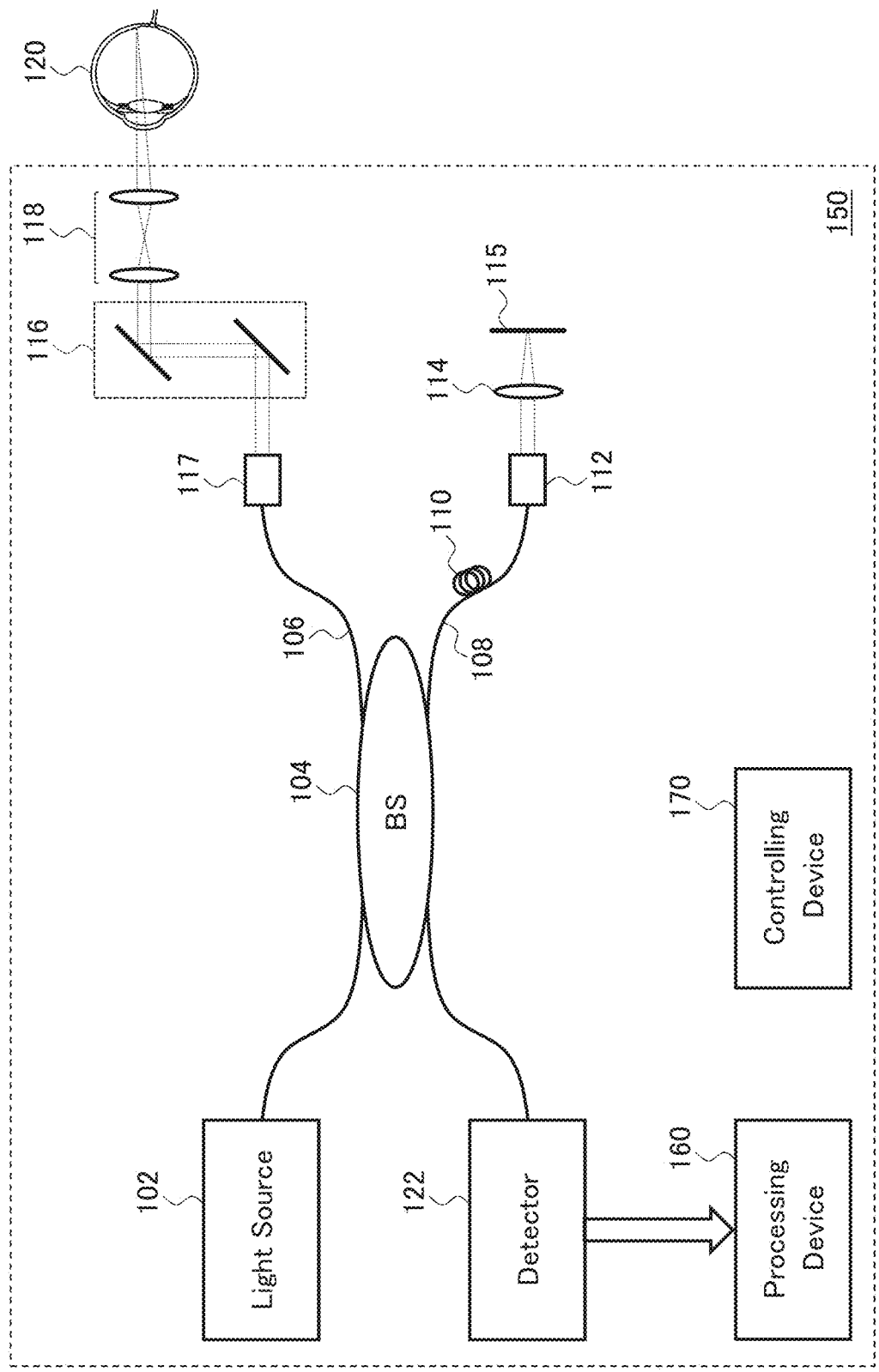
FIG. 8 is a schematic diagram illustrating the configuration of the ophthalmic apparatus (OCT apparatus) according to the exemplary aspect.
Figure 9:
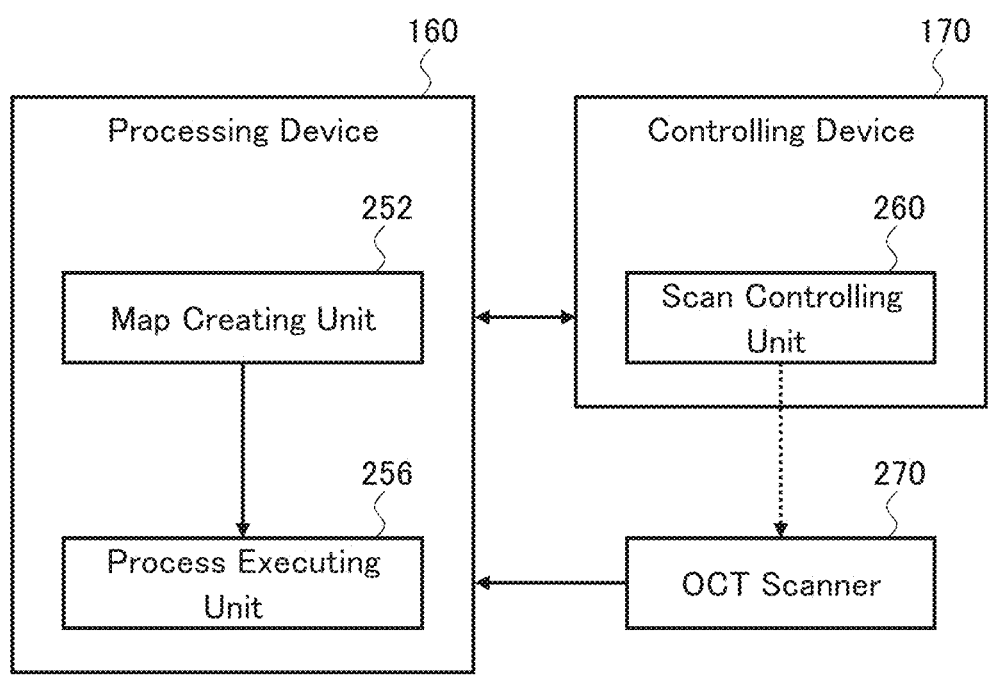
FIG. 9 is a schematic diagram illustrating the configuration of the ophthalmic apparatus according to the exemplary aspect.

FIGS. 8 and 9 show the configuration of the OCT apparatus (ophthalmic apparatus) 150 according to one exemplary aspect. The ophthalmic apparatus 150 provides OCT data processing in addition to OCT imaging.

The ophthalmic apparatus 150 is configured to apply OCT scans to a sample (eye) and acquire the first three dimensional data set and the second three dimensional data set. The area (target) to which an OCT scan is applied to acquire the first three dimensional data set is referred to as the first three dimensional region, and the area (target) to which an OCT scan is applied to acquire the second three dimensional data set is referred to as the second three dimensional region. The first three dimensional region and the second three dimensional region may coincide with each other, may partially coincide with each other, or may not have any common region. The ophthalmic apparatus 150 may acquire three or more three dimensional data sets. Thus, the ophthalmic apparatus 150 acquires at least two three dimensional data sets by applying OCT scans to the sample. Further, taking eye movements etc. into consideration, it is not necessary that a region to which an OCT scan targeting a certain three dimensional region is actually applied coincide with the three dimensional region itself. However, a region that substantially coincides with that three dimensional region may be scanned using an operation such as fixation or tracking.

Furthermore, the ophthalmic apparatus 150 is configured to create the first two dimensional map based on representative intensity values of a plurality of pieces of A-scan data included in the first three dimensional data set, and also create the second two dimensional map based on representative intensity values of a plurality of pieces of A-scan data included in the second three dimensional data set. The process of creating a two dimensional map from a three dimensional data set may be executed in the same manner as that of the first aspect example.

In addition, the ophthalmic apparatus 150 is configured to execute a process based on at least one of: at least the first partial data set of the first three dimensional data set; and at least the second partial data set of the second three dimensional data set. This process is executed on the basis of the first two dimensional map and the second two dimensional map. Hereinafter, the ophthalmic apparatus 150 thus configured will be described in more detail.

As shown in FIG. 8, the ophthalmic apparatus 150 includes the same optical element group as that of the ophthalmic apparatus 100 (see FIG. 1) of the first aspect example. The ophthalmic apparatus 150 includes the light source 102 that generates a light beam. The light source 102 is, for example, a broadband light source or a wavelength tunable light source. The beam splitter (BS) 104 splits a light beam emitted from the light source 102 into a sample light beam (measurement light) and a reference light beam (reference light). In other words, the beam splitter 104 directs part of the light beam emitted from the light source 102 to the sample arm 106 and another part to the reference arm 108.

The reference arm 108 includes the polarization controller 110 and the collimator 112. The polarization controller 110 is used for regulating the reference light beam, for example, for maximizing the interference efficiency. The collimator 112 outputs the reference light beam as a collimated light beam (parallel light beam). The reference light beam output from the collimator 112 is converted into a convergent light beam by the lens 114 and projected onto the reflecting mirror 115. The reference light beam reflected by the reflecting mirror 115 returns to the beam splitter 104 through the reference arm 108. The lens 114 and the reflecting mirror 115 are movable together, whereby the distance from the collimator 112 is changed (in other words, the path length of the reference light beam is changed).

The sample arm 106 guides the sample light beam via the collimator 117, the two dimensional scanner 116, and one or more objective lenses 118, and projects the sample light beam onto the eye 120 as a sample. The two dimensional scanner 116 is, for example, a galvano mirror scanner or a micro electro mechanical systems (MEMS) scanner. The return light of the sample light beam projected on the eye 120 returns to the beam splitter 104 through the sample arm 106. The two dimensional scanner 116 enables OCT scanning on a three dimensional region of the eye 120.

The beam splitter 104 generates an interference light beam by superposing the return light of the reference light beam and the return light of the sample light beam with one another. The interference light beam is guided to the detector 122 and detected by it. With this, the echo time delay of the light is measured from the interference spectrum.

The detector 122 generates a plurality of output sets, based on the composition (superposition) of the return light of the sample light beam supplied from the sample arm 106 and the return light of the reference light beam supplied from the reference arm 108. The result of the composition is interferogram data. For example, the output sets generated by the detector 122 may respectively correspond to light intensities received at different wavelengths output from the light source 102. When the sample light beam is projected sequentially to XY positions by the two dimensional scanner 116, the light intensities detected include information, for the XY positions, on reflection intensity distributions (back-scattering intensity distributions) from the inside region of the eye 120 along the depth direction (Z direction).

A three dimensional data set is obtained in the above-described manner. The three dimensional data set includes a plurality of pieces of A-scan data respectively corresponding to the XY positions. Each piece of A-scan data represents a spectral intensity distribution at a corresponding XY position. The three dimensional data set acquired by the detector 122 is sent to the processing device 160.

The processing device 160 is configured to execute the followings, for example: the creation of a two dimensional map based on the three dimensional data set; a process related to the three dimensional data set based on the two dimensional map. The processing device 160 includes a processor that operates according to a processing program. Some specific examples of the processing device 160 will be described later.

The controlling device 170 executes control of each part of the ophthalmic apparatus 150. For example, the controlling device 170 is configured to perform various controls to apply an OCT scan to a preset region of the eye 120. The controlling device 170 includes a processor that operates according to a control program. Some specific examples of the controlling device 170 will be described later.

Although not shown in the drawings, the ophthalmic apparatus 150 may further include a display device, an operation device, a communication device, and other elements.

The processing device 160 and the controlling device 170 will be further described with referring to FIG. 9. The processing device 160 includes the map creating unit 252, and the process executing unit 256. The controlling device 170 includes the scan controlling unit 260.

The OCT scanner 270 shown in FIG. 9 applies an OCT scan to the sample (the eye 120). The OCT scanner 270 of the present aspect includes, for example, the group of optical elements shown in FIG. 8, namely, the light source 102, the beam splitter 104, the sample arm 106 (the collimator 117, the two dimensional scanner 116, the objective lens 118, etc.), the reference arm 108 (the collimator 112, the lens 114, the reflecting mirror 115, etc.), and the detector 122. In some exemplary aspects, the OCT scanner may have other configurations.

The controlling device 170 executes control of each part of the ophthalmic apparatus 150. Control relating to OCT scanning, among various kinds of control, is performed by the scan controlling unit 260. The scan controlling unit 260 of the present aspect is configured to perform control for the OCT scanner 270. For example, the scan controlling unit 260 of the present aspect may be configured to perform control for the light source 102, control for the two dimensional scanner 116, and movement control for the lens 114 and the reflecting mirror 115. The scan controlling unit 260 includes a processor that operates according to a scan controlling program.

The processing device 160 executes various kinds of data processing such as computation, operation, calculation, analysis, measurement, and image processing. The map creating unit 252 and the process executing unit 252 respectively perform the two processes described above, namely, the creation of a two dimensional map based on a three dimensional data set, and the process related to the three dimensional data set based on the two dimensional map.

The map creating unit 252 includes a processor that operates according to a map creating program. The process executing unit 256 includes a processor that operates according to a process executing program.

The map creating unit 252 receives three dimensional data acquired from the eye 120 by an OCT scan, from the OCT scanner 270. In the present aspect, an OCT scan is performed by the OCT scanner 270 under the control of the scan controlling unit 260, targeting the first three dimensional region of the eye 120 set in advance, and an OCT scan is also performed by the OCT scanner 270 under the control of the scan controlling unit 260, targeting the second three dimensional region of the eye 120 set in advance. With these OCT scans, the first three dimensional data set and the second three dimensional data set are acquired and supplied to the map creating unit 252.

The map creating unit 252 creates the first two dimensional map based on representative intensity values respectively of a plurality of pieces of A-scan data included in the first three dimensional data set. The first three dimensional data set is data before being subjected to the imaging process (e.g., Fourier transform) by the image data generating unit 206. Each A-scan data is a spectral intensity distribution. The second two dimensional map is created from the second three dimensional data set in the same manner. The processing executed by the map creating unit 252 may be the same as that of the map creating unit 202 of the first aspect example.

The first two dimensional map and the second two dimensional map created by the map creating unit 252 are input to the process executing unit 256. Based on these two dimensional maps, the process executing unit 256 executes processing based on a partial data set of the first three dimensional data set and/or a partial data set of the second three dimensional data set. As in the first aspect example, the partial data set of the three dimensional data set in the present aspect may be part or all of the three dimensional data set.

Hereinafter, from among various kinds of processes executable by the process executing unit 256, described are examples of analysis, evaluation, setting of a region of interest (e.g., an analysis target region, evaluation target region), setting of an examination area, setting of an imaging area, comparison with examination data, registration, tracking, and panoramic OCT imaging (mosaic OCT imaging, montage OCT imaging). Note that, any two or more of these examples may be combined. The process executing unit 256 includes corresponding elements shown in two or more examples that are combined. For example, the process executing unit 256 may include some or all of the elements shown in FIGS. 10A to 16.

Figure 10A:
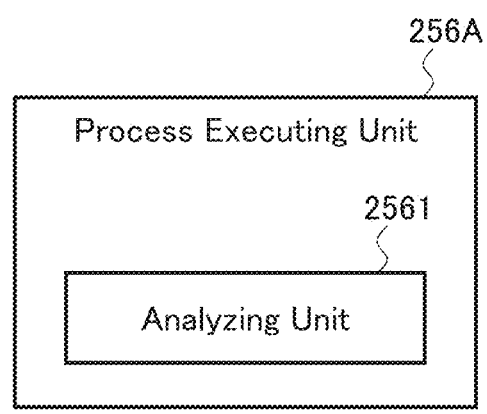
FIG. 10A is a schematic diagram illustrating the configuration of the ophthalmic apparatus according to the exemplary aspect.

The process executing unit 256A shown in FIG. 10A includes the analyzing unit 2561. the analyzing unit 2561 is configured to execute, based on the first two dimensional map and the second two dimensional map, a predetermined analysis process based on at least one of the first partial data set of the first three dimensional data set and the second partial data set of the second three dimensional data set.

For example, the analyzing unit 2561 performs a layer thickness analysis. The site on which the layer thickness analysis is to be performed may be any ocular tissue such as the followings: the retina; a sub-tissue of the retina; a combination of two or more sub-tissues of the retina; the choroid; a sub-tissue of the choroid; a combination of two or more sub-tissues of the choroid; the cornea; a sub-tissue of the cornea; a combination of two or more sub-tissues of the cornea; and the crystalline lens. The layer thickness analysis includes, for example, segmentation and thickness measurement. The segmentation is a process of identifying a region of the three dimensional data set (a partial data set) corresponding to the target sites mentioned above. The thickness measurement is a process of measuring the thickness of the identified partial data set at one or more measurement positions.

The analyzing unit 2561 may be configured to be capable of executing the same placement process executed by the placing unit 204 of the first aspect example. Based on a result of the placement process, the analyzing unit 2561 may determine the positions in the eye 120 respectively corresponding to the layer thickness measurement positions. This makes it possible to grasp at which positions, locations or sites in the eye 120 the layer thickness measurement has been performed.

The analyzing unit 2561 may apply the layer thickness analysis described above to at least one of the first partial data set and the second partial data set. The layer thickness analysis applied one of the first partial data set and the second partial data set may be the same as the layer thickness analysis of the first aspect example, for example.

In the event that the layer thickness analysis is applied to both the first partial data set and the second partial data set, and also in the event that at least part of the region of the eye 120 corresponding to the first partial data set and at least part of the region of the eye 120 corresponding to the second partial data set overlap with one another, the analyzing unit 2561 may determine a change in the layer thickness in the overlapped regions (common regions), for example. Put differently, the analyzing unit 2561 may determine the difference (e.g., difference or ratio) between the layer thickness of the common region derived from the first partial data set and the layer thickness of the common region derived from the second partial data set. In the case where the time point at which the first three dimensional data set is acquired is different from the time point at which the second three dimensional data set is acquired, the difference between the layer thicknesses of the common regions obtained in this way represents the change in the layer thickness over time.

The above example describes the chronological variation of a predetermined parameter value (e.g., layer thickness value) based on the two three dimensional data sets (i.e., the first three dimensional data set and the second three dimensional data set) acquired at different time points. However, a time course analysis similar to the above example may be performed based on three or more three dimensional data sets.

In the event that the layer thickness analysis is applied to both the first partial data set and the second partial data set is described, and also in the event that at least part of the region of the eye 120 corresponding to the first partial data set is different from at least part of the region of the eye 120 corresponding to the second partial data set, the analyzing unit 2561 may create a layer thickness distribution of a wider area by composing a layer thickness distribution based on the first partial data set and a layer thickness distribution based on the second partial data set, for example.

The analysis process executable by the analyzing unit 2561 is not limited to such layer thickness analysis. Another example is size analysis to measure the size of a tissue. The tissue to be measured by the size analysis may be the optic nerve head, a lesion, or a blood vessel. Cup diameter, disk diameter, rim diameter, depth, etc. may be measured for the optic nerve head. Area, volume, length, etc. may be measured for a lesion. Thickness, length, etc. may be measured for a blood vessel. The size analysis includes, for example, segmentation and measurement. Here, the segmentation is a process of identifying a region of the three dimensional data set (a partial data set) corresponding to such a target tissue. The measurement is a process of measuring the size of the partial data set identified. Any of the above matters regarding the layer thickness analysis may be applied to the size analysis.

Another example of the analysis process is shape analysis for measuring the shape of a tissue. The tissue to be subjected to the shape analysis may be, for example, the optic nerve head, a lesion, a blood vessel, or other tissues. The shape analysis includes, for example, segmentation and shape specification. Here, the segmentation is a process of identifying a region of the three dimensional data set (a partial data set) corresponding to such a target tissue. The shape specification is a process of determining the shape of the partial data set identified. The shape specification includes, for example, a process of extracting the contour of the identified partial data set and a process of specifying the shape of the contour (e.g., circularity, roundness, ellipticity, cylindricity, etc.). Any of the above matters regarding the layer thickness analysis may be applied to the shape analysis.

In addition to the shape measurement described above, orientation analysis may be performed. The orientation analysis is a process of measuring the orientation of a target tissue. The orientation analysis may include, for example, a process of determining a figure that approximates the contour shape of the identified partial data set (e.g., an approximate ellipse), and a process of determining the orientation of the approximate figure (e.g., the orientation of the major axis of the approximate ellipse). In another example, the orientation analysis includes a process of calculating a specific parameter of the identified partial data set (e.g., the maximum diameter), and a process of determining the orientation based on the calculated parameter (e.g., the orientation of a line segment indicating the maximum diameter).

Figure 10B:
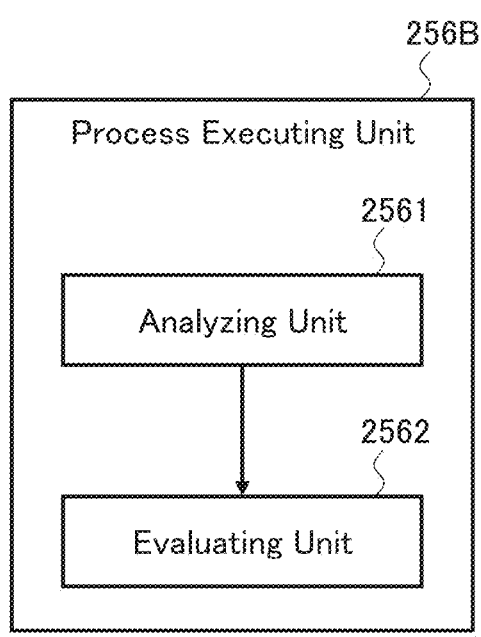
FIG. 10B is a schematic diagram illustrating the configuration of the ophthalmic apparatus according to the exemplary aspect.

The process executing unit 256B shown in FIG. 10B includes the analyzing unit 2561 and the evaluating unit 2562. The analyzing unit 2561 is configured to execute a predetermined analysis process based on at least one of the first partial data set of the first three dimensional data set and the second partial data set of the second three dimensional data set. The evaluating unit 2062 is configured to execute a predetermined evaluation process based on data obtained by the analysis process. The analyzing unit 2561 may be the same as the analyzing unit 2561 in FIG. 10A.

For example, the evaluating unit 2562 compares the data obtained by the analyzing unit 2561 with normative data. By so doing, the evaluating unit 2562 can evaluate whether or not the data for the eye 120 is normal (i.e., whether or not there is a suspected disease), determine the degree or stage of disease, or determine the degree of suspicion of disease.

The evaluation process is not limited to such normative data comparison, and may include any evaluation processing using statistics, any evaluation processing using computations or operations, or the like.

A combination of the analysis process and the evaluation process applied to one of the first partial data set and the second partial data set may be, for example, the same as any of the combinations of the analysis process and the evaluation process described in the first aspect example.

In the event that a combination of the analysis process and the evaluation process is applied to both the first partial data set and the second partial data set, the process executing unit 256B may determine the chronological variation of analysis data, and may also determine the chronological variation of evaluation based on the chronological variation of analysis data, for example.

Figure 10C:
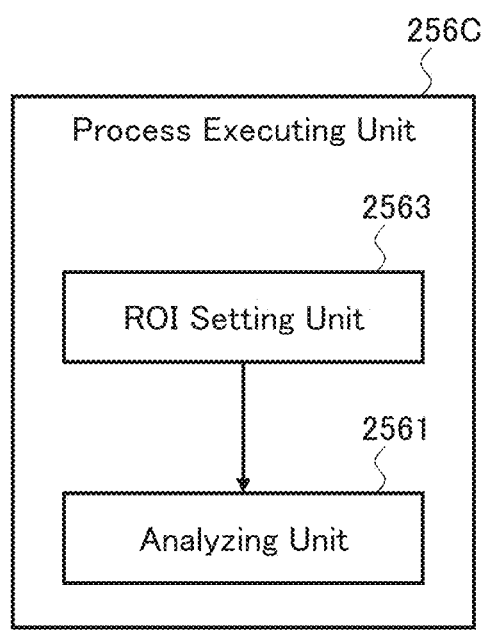
FIG. 10C is a schematic diagram illustrating the configuration of the ophthalmic apparatus according to the exemplary aspect.

The process executing unit 256C shown in FIG. 10C includes the region of interest (ROI) setting unit 2563 and the analyzing unit 2561. The ROI setting unit 2563 is configured to set a partial data set to which an analysis process is to be applied. The partial data set is a region of interest that is at least part of the three dimensional data set. The analyzing unit 2561 is configured to execute a predetermined analysis process based on the partial data set defined by the ROI setting unit 2563. The analyzing unit 2561 may be the same as the analyzing unit 2561 in FIG. 10A.

The ROI setting unit 2563 sets a region of interest by analyzing the three dimensional data set, for example. The setting of a region of interest includes, for example, segmentation for identifying a region of interest in the three dimensional data set. In the present example, the ROI setting unit 2563 sets the first region of interest in the first three dimensional data set and the second region of interest in the second three dimensional data set. The region of the eye 120 corresponding to the first region of interest may be the same as or different from the region of the eye 120 corresponding to the second region of interest.

In another example, the controlling device 170 displays a two dimensional map (or any image based on a three dimensional data set) on a display device (not shown in the drawings). The user designates a desired region in the displayed two dimensional map (or the displayed image) using an operation device (not shown in the drawings). The ROI setting unit 2563 may set a region of interest in the three dimensional data set based on the region designated by the user in the displayed two dimensional map (or the displayed image). Thereby, the first region of interest is set in the first three dimensional data set, and the second region of interest is set in the second three dimensional data set.

The region of the eye corresponding to the region of interest may include, for example, any of the followings: lesion; blood vessel; optic nerve head; macula; sub-tissue of eye fundus (e.g., inner limiting membrane, nerve fiber layer, ganglion cell layer, inner plexiform layer, inner nuclear layer, outer plexiform layer, outer nuclear layer, external limiting membrane, photoreceptor layer, retinal pigment epithelium layer, Bruch membrane, choroid, sclera, etc.); sub-tissue of cornea (e.g., corneal epithelium, Bowman's membrane, corneal stroma, Dua's layer, Descemet's membrane, corneal endothelium, etc.); iris; crystalline lens; Zinn's zonule; ciliary body; vitreous body; and other ocular tissues.

The evaluating unit 2562 may be combined with the process executing unit 256C shown in FIG. 10C. The evaluating unit 2562 of the present example executes a predetermined evaluation process, based on the data obtained by the analysis process executed by the analyzing unit 2561 on the basis of the first region of interest and the second region of interest (i.e., the first partial data set and second partial data set) set by the ROI setting unit 2563. The evaluating unit 2562 in the present example may be the same as the evaluating unit 2562 in FIG. 10B.

Figure 10D:
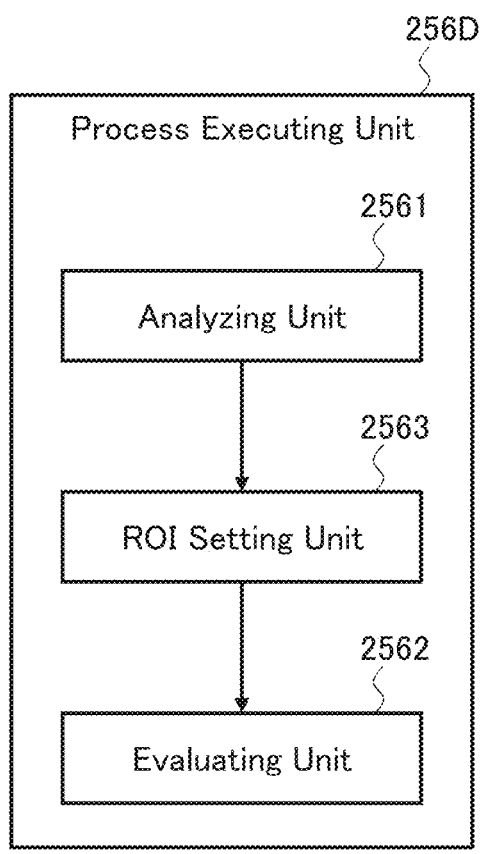
FIG. 10D is a schematic diagram illustrating the configuration of the ophthalmic apparatus according to the exemplary aspect.

The process executing unit 256D shown in FIG. 10D includes the analyzing unit 2561, the ROI setting unit 2563, and the evaluating unit 2562. The analyzing unit 2561 is configured to perform a predetermined analysis process based on at least one of the first partial data set of the first three dimensional data set and the second partial data set of the second three dimensional data set. The ROI setting unit 2563 is configured to set partial data of the data acquired by the analysis process, to which an evaluation process is to be applied. The partial data is a region of interest that is at least part of the analysis data. The evaluating unit 2562 is configured to perform a predetermined evaluation process, based on at least one of: the first region of interest set for the analysis data obtained from the first partial data set; and the second region of interest set for the analysis data obtained from the second partial data set. The analyzing unit 2561 may be the same as the analyzing unit 2561 in FIG. 10A. The evaluating unit 2562 may be the same as the evaluating unit 2562 in FIG. 10B.

The ROI setting unit 2563, for example, identifies a partial data set of a three dimensional data set by analyzing the three dimensional data set, and sets, as a region of interest, partial data of analysis data corresponding to the identified partial data set. The setting of the partial data set includes, for example, segmentation.

In another example, the ROI setting unit 2563 sets a region of interest by analyzing the analysis data obtained by the analyzing unit 2561. As an example, the ROI setting unit 2563 performs a process of detecting characteristic partial data in the analysis data, and a process of setting a region of interest based on the partial data detected.

In yet another example, the controlling device 170 displays a two dimensional map on a display device (not shown in the drawings). Alternatively, the controlling device 170 displays any image based on a three dimensional data set or analysis data on the display. The user designates a desired region in the displayed two dimensional map (or, the displayed image or the displayed analysis data) using an operation device (not shown in the drawings). The ROI setting unit 2563 may set a region of interest in analysis data based on the region designated by the user in the displayed two dimensional map (or, the displayed image or the displayed analysis data).

Figure 11:
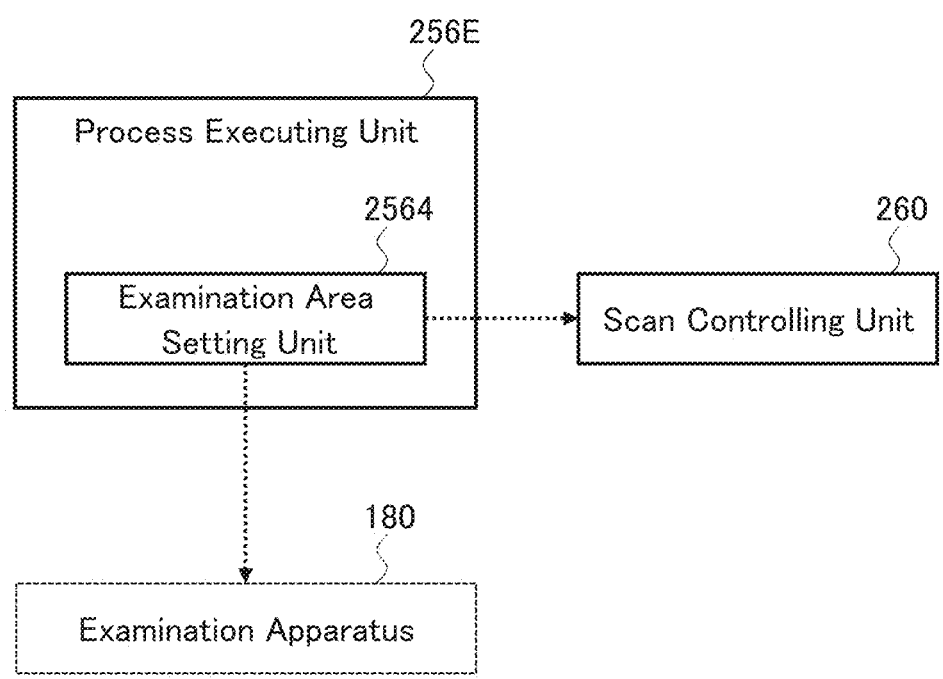
FIG. 11 is a schematic diagram illustrating the configuration of the ophthalmic apparatus according to the exemplary aspect.

The process executing unit 256E shown in FIG. 11 includes the examination area setting unit 2564 configured to execute the setting of an area to which a predetermined examination is to be applied (examination area) for the eye 120. The predetermined examination may be any examination such as OCT scanning, visual field examination, microperimetry, electrophysiological examination, or the like.

For example, the examination area setting unit 2564 performs the following processes: a process of determining a site that requires attention (a site requiring attention) of the eye 120 by analyzing any one or more of a two dimensional map, a three dimensional data set, and data generated based on at least one of the two dimensional map and the three dimensional data set; and a process of setting an examination area based on the site requiring attention determined. The site requiring attention is, for example, a lesion, a specific site, a specific tissue, or the like. Typically, the examination area is set to include at least part of the site requiring attention.

In one example, the examination area setting unit 2564 performs the following processes: segmentation on a two dimensional map (or a three dimensional data set); a process of converting the region in the two dimensional map identified by the segmentation into the site requiring attention in the eye 120, based on the result of the placement process described above; and a process of setting an examination area based on the site requiring attention.

In the event that the examination area set by the examination area setting unit 2564 is an area to which OCT scanning is applied, information indicating the examination area may be provided to the scan controlling unit 260. The scan controlling unit 260 controls the OCT scanner 270 to apply an OCT scan to this examination area.

In the event that the examination area set by the examination area setting unit 2564 is an area to which an OCT scan is applied, information indicating the examination area may be provided to another OCT apparatus (the examination apparatus 180) via the communication device described above.

In the event that the examination area set by the examination area setting unit 2564 is an area to which a certain examination is applied, information indicating the examination area may be provided to the examination apparatus 180 corresponding to the examination via the communication device described above.

In the event that the examination area setting unit 2564 processes only one of the first partial data set of the first three dimensional data set and the second partial data set of the second three dimensional data set, the processing executed by the examination area setting unit 2564 may be the same as that executed by the examination area setting unit 2064 in the first aspect example.

In the event that the examination area setting unit 2564 processes both the first partial data set of the first three dimensional data set and the second partial data set of the second three dimensional data set, the examination area setting unit 2564 may set the first examination area based on the first partial data set and the second examination area based on the second partial data set. Then, the examination area setting unit 2564 may set an examination area of a wider area by composing the first examination area and second examination area.

Figure 12:
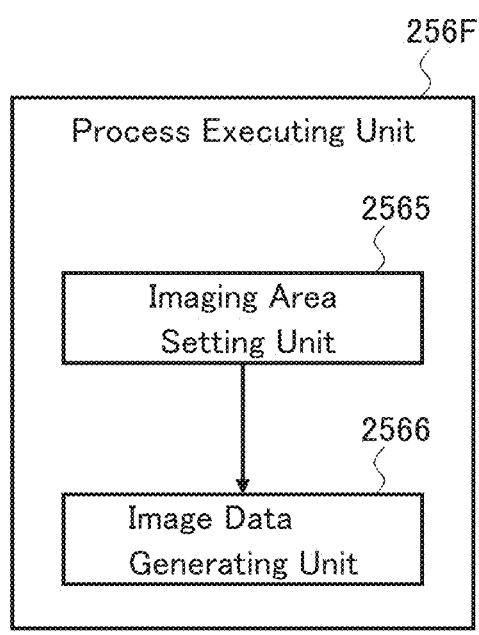
FIG. 12 is a schematic diagram illustrating the configuration of the ophthalmic apparatus according to the exemplary aspect.

The process executing unit 256F shown in FIG. 12 includes the imaging area setting unit 2565 and the image data generating unit 2566. The imaging area setting unit 2565 is configured to set a partial data set to which the imaging process is to be applied. Here, the partial data set is an imaging area that is at least part of the three dimensional data set. The image data generating unit 2566 is configured to generate image data of the imaging area set defined by the imaging area setting unit 2565.

The imaging process includes at least Fourier transform. Examples of the imaging process include general OCT image construction, motion contrast (OCT angiography, etc.), phase image construction, polarization image construction, and the like.

For example, the imagining area setting unit 2565 performs the following processes: a process of determining a site requiring attention of the eye 120 by analyzing any one or more of a two dimensional map, a three dimensional data set, and data generated based on at least one of the two dimensional map, and the three dimensional data set; and a process of setting an imaging area based on the site requiring attention determined. The site requiring attention is, for example, a lesion, a specific site, a specific tissue, or the like. Typically, the imaging area is set to include at least part of the site requiring attention.

In one example, the imaging area setting unit 2565 performs the following processes: segmentation on a two dimensional map (or a three dimensional data set); a process of converting the region in the two dimensional map identified by the segmentation into the site requiring attention in the eye 120 based on the result of the placement process; and a process of setting an imaging area based on the site requiring attention.

The image data generating unit 2566 is configured to generate image data based on data acquired by the OCT scanner 270. For example, the image data generating unit 2566 constructs image data of a cross sectional image of the eye 120 based on the output from the OCT scanner 270. The output from the OCT scanner 270 is referred to as sampled data or interference signal data. Such image data generating processing includes filtering, fast Fourier transform (FFT), etc. as in conventional OCT techniques (e.g., swept source or spectral domain OCT technique). With such processing, reflection intensity profiles are acquired for the A-lines respectively corresponding to the XY positions, and a group of image data for the A-lines is constructed by performing the imaging process on the reflection intensity profiles. Here, an A-line is a scan path of the measurement light beam in the eye 120, and a reflection intensity profile lies along the Z direction. In addition, image data for an A-line is referred to as A-scan image data.

Furthermore, the image data generating unit 2566 may be configured to construct a plurality of pieces of A-scan image data according to the OCT scan mode, and then construct two dimensional image data or three dimensional image data by arranging the plurality of pieces of A-scan image data. The OCT scan mode is concerned with, for example, measurement light beam deflection and A-scan position transition.

In the case where a plurality of pieces of cross sectional image data is obtained by raster scan or another scan mode, the image data generating unit 2566 may construct stack data by embedding the plurality of pieces of cross sectional image data in a single three dimensional coordinate system. In addition, the image data generating unit 2566 may construct voxel data (volume data) by applying voxelization to the stack data.

The image data generating unit 2566 may be configured to perform rendering on the stack data or the volume data. A rendering technique applied thereto is optional. For example, any of volume rendering, multi planar reconstruction (MPR), surface rendering, and other rendering techniques may be applied thereto. Furthermore, the image data generating unit 2566 may be configured to construct a planar image from the stack data or the volume data. Examples of the planar image include a front image and en-face image. For example, the image data generating unit 2566 may be configured to construct a projection image by integrating the stack data or the volume data along their A-lines.

In the present example, the image data generating unit 2566 generates image data by applying the imaging process to an OCT data set (i.e., a partial data set of the three dimensional data set) included in the imaging area set by the imaging area setting unit 2565.

In another example, the image data generating unit 2566 generates image data by applying the imaging process to the three dimensional data set. Further, the process executing unit 256F extracts partial image data corresponding to the imaging area set by the imaging area setting unit 2565, from the image data generated by the image data generating unit 2566. The extraction of the partial image data may be performed, for example, by clipping, cropping or trimming.

The process executing unit 256F shown in FIG. 12 has the image constructing function (the image data generating unit 2566); however, OCT apparatuses (ophthalmic apparatuses) of other exemplary aspects may not have the image constructing function. In this case, information indicating the imaging area set by the imaging area setting unit 2565 may be provided to an external device (including an imaging processor) via a communication device (not shown in the drawings).

In the event that the process executing unit 256F processes only one of the first partial data set of the first three dimensional data set and the second partial data set of the second three dimensional data set, the processing may be performed in the same manner as that of the process executing unit 206F in the first aspect example.

In the event that the process executing unit 256F processes both the first partial data set of the first three dimensional data set and the second partial data set of the second three dimensional data set, the imaging area setting unit 2565 sets the first imaging area based on the first partial data set and the second imaging area based on the second partial data set. By composing the first imaging area and the second imaging area, the imaging area setting unit 2565 may set a wider imaging area.

Figure 13:
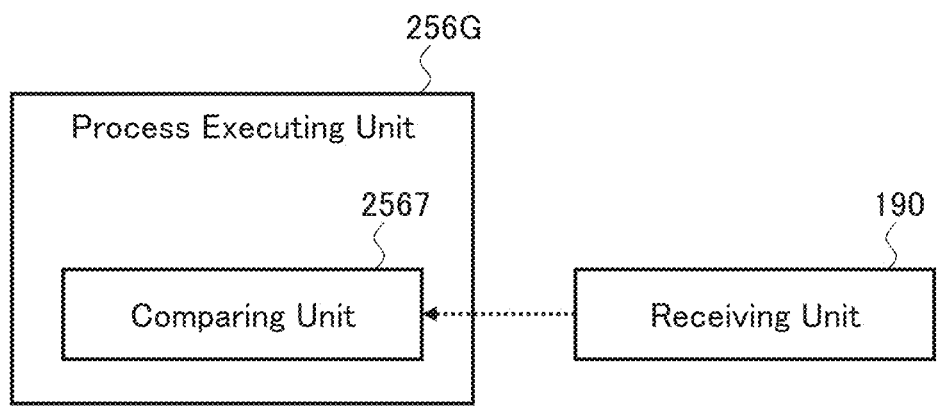
FIG. 13 is a schematic diagram illustrating the configuration of the ophthalmic apparatus according to the exemplary aspect.

The example shown in FIG. 13 is provided with the receiving unit 190. The receiving unit 190 is configured to receive data (examination data) acquired from the eye 120 by a predetermined examination different from OCT. Further, the process executing unit 256G of the present example includes the comparing unit 2567. The comparing unit 2567 is configured to execute a predetermined comparison process between at least part of the examination data received by the receiving unit 190 and at least part of the three dimensional data set acquired by the OCT scanner 270.

The receiving unit 190 receives examination data obtained from the eye 120, from the outside (e.g., an ophthalmic apparatus, an image archiving system, a recording medium). The receiving unit 190 may include a communication device or a drive device, for example.

The examination data may be data obtained by any modality or examination. Examples of examination data include sensitivity distribution data obtained by visual field examination of the eye 120, electroretinogram (EGR) obtained by electrophysiological examination, tear film distribution data obtained by tear film photography (anterior eye segment photography), etc.

The comparing unit 2567 may be configured to perform the followings, for example: the placement process same as that performed by the placing unit 204; registration between the two dimensional map based on the result of the placement process and the examination data; registration between the examination data and a three dimensional data set based on the result of the prior registration; and a predetermined comparison process based on the examination data and the three dimensional data set (at least a part thereof) to which the registration has been performed.

The comparison process may include any one or more of the following comparisons, for example: a comparison between a three dimensional data set and examination data; a comparison between a two dimensional map created based on a three dimensional data set and examination data; a comparison between image data constructed based on a three dimensional data set and examination data; a comparison between analysis data of a two dimension map and examination data; a comparison between analysis data of image data and examination data; a comparison between a three dimensional data set and processed data of examination data; a comparison between a two dimensional map created based on a three dimensional data set and processed data of examination data; a comparison between image data constructed based on a three dimensional data set and processed data of examination data; a comparison between analysis data of a two dimensional map and processed data of examination data; and a comparison between analysis data of image data and processed data of examination data.

In the event that the comparing unit 2567 processes only one of the first partial data set of the first three dimensional data set and the second partial data set of the second three dimensional data set, the processing may be performed in the same manner as that of the comparing unit 2067 in the first aspect example.

In the event that the comparing unit 2567 processes both the first partial data set of the first three dimensional data set and the second partial data set of the second three dimensional data set, the comparing unit 2567 may perform a comparison process based on the first partial data set and a comparison process based on the second partial data set, and then obtain a comparison result for a wider area by composing the two results obtained by the two comparison processes.

Figure 14:
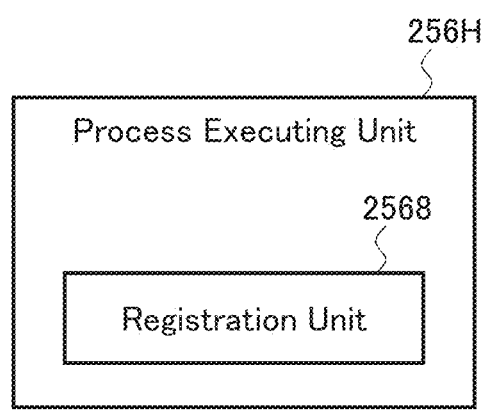
FIG. 14 is a schematic diagram illustrating the configuration of the ophthalmic apparatus according to the exemplary aspect.

The process executing unit 256H shown in FIG. 14 includes the registration unit 2568. The registration unit 2568 is configured to perform registration between the first partial data set and the second partial data set, by executing registration between the first two dimensional map created based on the first three dimensional data set and the second two dimensional map created based on the second three dimensional data set.

The registration unit 2568 first compares the first two dimensional map and the second two dimensional map with each other. Based on the result of the comparison, the registration unit 2568 performs registration between the first two dimensional map and the second two dimensional map.

The comparison of the two dimensional maps may include an image correlation calculation. One of the techniques adoptable to the image correlation calculation is described in Japanese Patent No. 6,276,943 (International Patent Publication No. WO2015/029675). In the case of employing this technique, the registration unit 2568 may be configured to apply phase only correlation (POC) to the set of the first two dimensional map and the second two dimensional map, thereby calculating a positional difference amount between the first two dimensional map and the second two dimensional map. The positional difference amount includes, for example, any one or both of a translation amount and a rotation amount. The registration is performed to adjust the relative position between the first two dimensional map and the second two dimensional map to compensate for (or, cancel or eliminate) the positional difference amount calculated.

For details of such a two dimensional map comparing technique with phase only correlation, Japanese Patent No. 6,276,943 (International Patent Publication No. WO2015/029675) may be referred to. Further, the two dimensional map comparing technique adopted hereto is not limited to the above-described example, and any technique within the scope of the invention described in Japanese Patent No. 6,276,943 (International Patent Publication No. WO2015/029675) or any modification thereof may be applied hereto. Furthermore, any kinds of image correlation other than phase only correlation may be used, and further any kinds of image comparison other than image correlation may be used, in order to implement the two dimensional map comparison of the present example.

Figure 15:
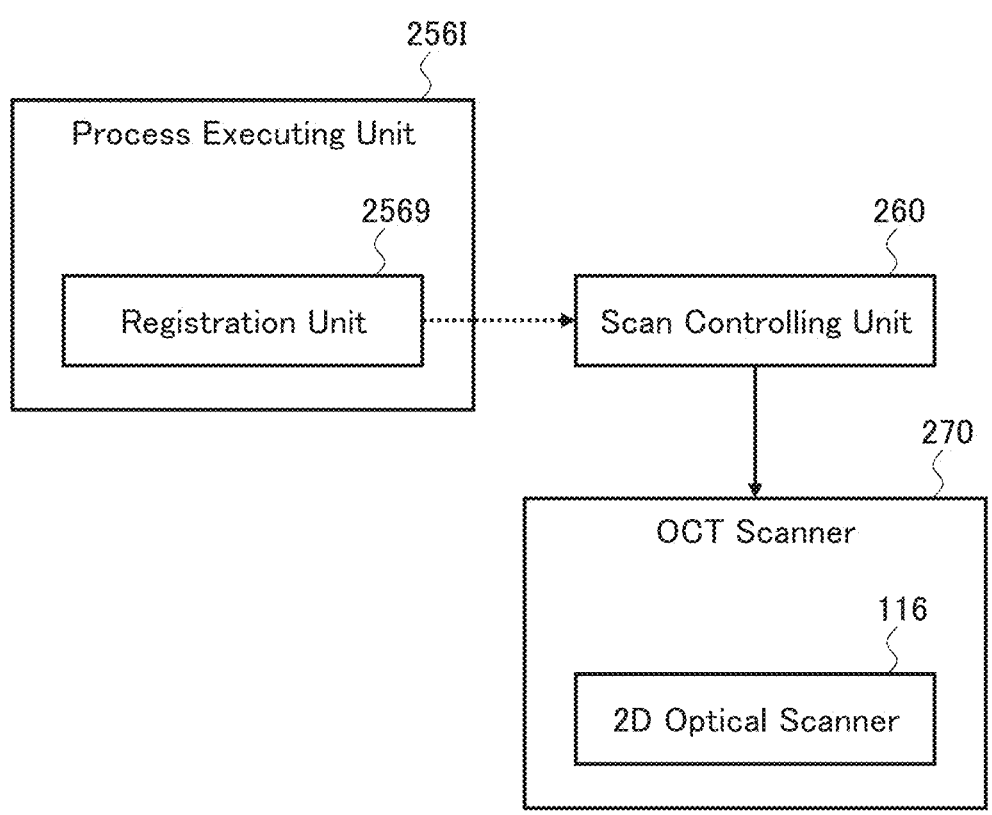
FIG. 15 is a schematic diagram illustrating the configuration of the ophthalmic apparatus according to the exemplary aspect.

The process executing unit 2561 shown in FIG. 15 includes the registration unit 2569. The registration unit 2569 is configured to perform registration between the first two dimensional map created based on the first three dimensional data set and the second two dimensional map created based on the second three dimensional data set.

In the same manner as the registration unit 2568 of FIG. 14, the registration unit 2569 compares the first two dimensional map and the second two dimensional map and performs registration between the first two dimensional map and the second two dimensional map based on the result of the comparison. The comparison of these two dimensional maps includes, for example, an image correlation calculation. The image correlation calculation may include a phase only correlation calculation. The phase only correlation calculation may be executed to derive the amount of positional difference between the first two dimensional map and the second two dimensional map. The positional difference amount includes, for example, any one or both of a translation amount and a rotation amount. The registration is executed to change the relative position between the first two dimensional map and the second two dimensional map to compensate for the positional difference amount calculated. The registration method or technique is not limited to the above-described examples.

The output from the registration unit 2569 (i.e., information indicating the positional difference amount between the first two dimensional map and the second two dimensional map) is input to the scan controlling unit 260. The scan controlling unit 260 adjusts the area to which an OCT scan is applied for the eye 120, based on the information input from the registration unit 2569. For example, the scan controlling unit 260 modulates the control signals fed to be sent to the two dimensional optical scanner 116 so as to compensate for the positional difference amount between the first two dimensional map and the second two dimensional map.

Typically, the OCT scanner 270 sequentially acquires three dimensional data sets by repeatedly applying OCT scans to the eye 120. The sequentially-acquired three dimensional data sets are input to the processing device 160 in a sequential manner (e.g., in real time). The map creating unit 252 creates two dimensional maps sequentially (e.g., in real time) from the sequentially-input three dimensional data sets. The sequentially-created two dimensional maps are input to the registration unit 2569 in a sequential manner (e.g., in real time). The registration unit 2569 applies the above-mentioned registration sequentially (e.g., in real time) to the sequentially-input two dimensional maps. For example, the registration unit 2569 applies registration to a set of the n-th input two dimensional map and the (n+1)-th input two dimensional map (where n is a positive integer). Thereby, the positional difference amount between two consecutive two dimensional maps is obtained substantially in real time. In other words, the displacement (positional difference) between the position of the eye 120 at the time point when the n-th three dimensional data set is acquired and the position of the eye 120 at the time point when the (n+1)-th three dimensional data set is acquired, is obtained substantially in real time. The positional difference amounts acquired in a sequential manner are input sequentially (e.g., in real time) to the scan controlling unit 260. The scan controlling unit 260 sequentially modulates the control signals fed to the two dimensional optical scanner 116 so as to compensate for the sequentially-input positional difference amounts. By the iteration of such a series of real-time processes, areas to which OCT scans are sequentially applied is adjusted in a sequential manner according to the movement of the eye 120. Such an adjustment operation is referred to as tracking.

Figure 16:
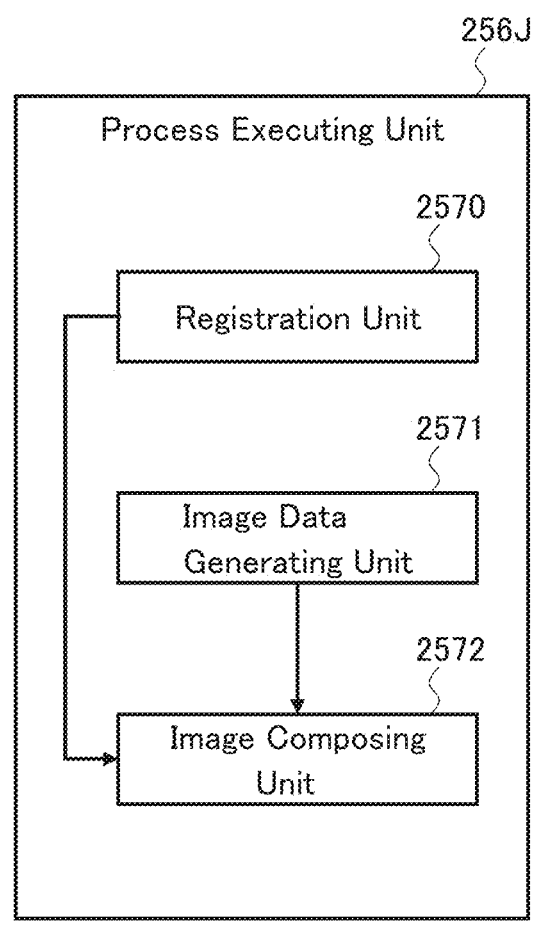
FIG. 16 is a schematic diagram illustrating the configuration of the ophthalmic apparatus according to the exemplary aspect.

In the example shown in FIG. 16, the first three dimensional data set and the second three dimensional data set are acquired from mutually different three dimensional regions of the eye 120. That is, the first three dimensional data set is acquired from the first three dimensional region of the eye 120, and the second three dimensional data set is acquired from the second three dimensional region that is different from the first three dimensional region. Typically, part of the first three dimensional region overlaps with part of the second three dimensional region.

The process executing unit 256J shown in FIG. 16 includes the registration unit 2570, the image data generating unit 2571, and the image composing unit 2572.

The registration unit 2570 is configured to perform registration between the first two dimensional map created based on the first three dimensional data set and the second two dimensional map created based on the second three dimensional data set. The processing executed by the registration unit 2570 may be the same as that executed by the registration unit 2569 in FIG. 15.

The image data generating unit 2571 generates the first image data from the first partial data set of the first three dimensional data set, and the second image data from the second partial data set of the second three dimensional data set. The processing executed by the image data generating unit 2571 may be the same as that executed by the image data generating unit 2066 in FIG. 12.

The image composing unit 2572 composes the first image data and the second image data generated by the image data generating unit 257, based on the result of the registration between the first two dimensional map and the second two dimensional map obtained by the registration unit 2570.

The result of registration between the first two dimensional map and the second two dimensional map includes a relative positional difference amount between the first two dimensional map and the second two dimensional map. The relative positional difference amount indicates a relative positional relationship between the first two dimensional map and the second two dimensional map. The relative positional relationship between the first two dimensional map and the second two dimensional map corresponds to the relative positional relationship between the first three dimensional data set and the second three dimensional data set (in particular, the relative positional relationship in the XY plane). The image composing unit 2572 arranges (or, aligns or places) the first image data and the second image data according to the relative positional relationship, and composes the first image data and the second image data arranged.

The relative positional relationship in the Z direction between the first three dimensional data set and the second three dimensional data set may be determined, for example, by analyzing the first three dimensional data set and the second three dimensional data set. Alternatively, the relative positional relationship in the Z direction between the first three dimensional data set and the second three dimensional data set may be determined by analyzing the first image data and the second image data. For example, the registration between the first image data and the second image data may be performed by performing registration of the common regions (overlapped regions) between the first image data and the second image data.

In another example, in the event that acquired is the third three dimensional data set that includes at least part of the first three dimensional data set and at least part of the second three dimensional data set, registration between the first three dimensional data set (or, the first two dimensional map, the first image data or other data) and the second three dimensional data set (or, the second two dimensional map, the second image data or other data) may be performed via the third three dimensional data set or processed data thereof (e.g., two dimensional map, image data or other data).

The processing device 160 may be capable of performing various kinds of data processing other than the data processing described above. The processing device 160 may be configured to process data acquired by OCT scanning (OCT data). The OCT data is, for example, interference signal data, reflection intensity profiles, or image data. Note that the interference signal data is at least part of the three dimensional data set.

The processing device 160 may be capable of processing data other than OCT data. For example, in the event that the ophthalmic apparatus 150 includes a data acquisition device other than the OCT scanner 270, the processing device 160 may be configured to process data acquired by the data acquisition device. An ophthalmic apparatus adoptable to the data acquisition device may be any ophthalmic imaging apparatus such as a fundus camera, scanning laser ophthalmoscope (SLO), surgical microscope, or slit lamp microscope. An ophthalmic apparatus adoptable to the data acquisition device may be any ophthalmic measurement apparatus such as a refractometer, keratometer, tonometer, eye axial length measurement device, specular microscope, wave front analyzer, or perimeter. Further, in the event that the OCT apparatus is a medical apparatus of any kind, that is, in the event that the OCT apparatus is an apparatus used in any medical department, the medical apparatus adopted as the data acquisition device may be a medical imaging apparatus of any kind and/or medical examination apparatus of any kind. In addition, an OCT apparatus used in any field other than medical care includes a data acquisition device corresponding to the application field.

Several examples of operations that may be performed by the ophthalmic apparatus 150 having the configuration exemplified above will be described.

Figure 17:
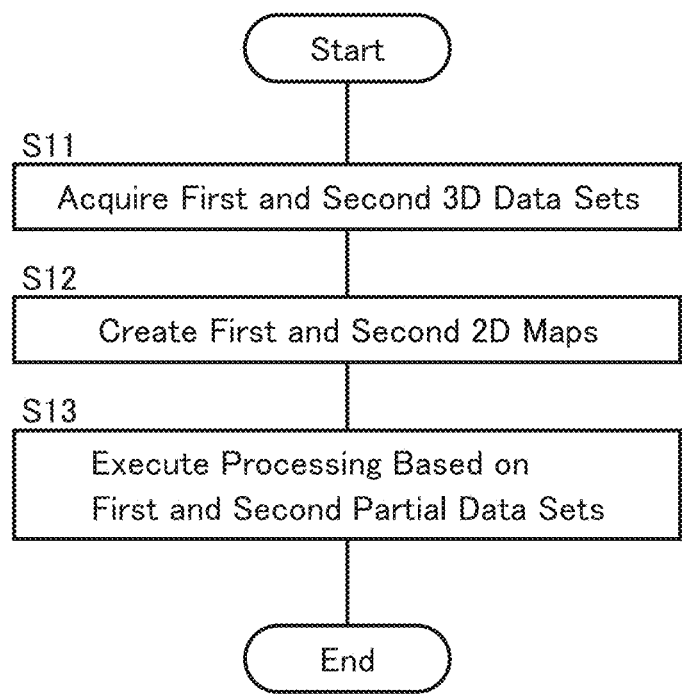
FIG. 17 is a flowchart illustrating the operation of the ophthalmic apparatus according to the exemplary aspect.

Moving now on to FIG. 17. In the present example, first, the scan controlling unit 260 controls the OCT scanner 270 to acquire the first three dimensional data set and the second three dimensional data set by applying OCT scans to the eye 120 (S11). More generally, two or more three dimensional data sets may be acquired.

Next, the map creating unit 252 creates the first two dimensional map based on representative intensity values respectively of a plurality of pieces of A-scan data included in the first three dimensional data set acquired in step S11, and also creates the second two dimensional map based on representative intensity values respectively of a plurality of pieces of A-scan data included in the second three dimensional data set acquired in step S11 (S12).

Next, based on the first two dimensional map and the second two dimensional map created in step S12, the process executing unit 256 executes a predetermined process on the basis of at least one of the first partial data set of the first three dimensional data set and the second partial data set of the second three dimensional data set acquired in step S11.

The process executed in step S13 may include any one or more of the followings: predetermined analysis process; predetermined evaluation process; setting of a region of interest; setting of an examination area; setting of an imaging area; generation of image data; predetermined comparison process with examination data; registration; tracking; and panoramic OCT imaging. In other words, the process executing unit 256 may include any one or more of the followings: the analyzing unit 2561; the evaluating unit 2562; the ROI setting unit 2563; the examination area setting unit 2564; the imaging area setting unit 2565; the image data generating unit 2566; the comparing unit 2567; the registration unit 2568; the registration unit 2569; the registration unit 2570; the image data generating unit 2571; and the image composing unit 2572.

Some effects of the ophthalmic apparatus (OCT apparatus) 150 of the present aspect will be described.

The ophthalmic apparatus 150 according to the present embodiment includes the OCT scanner 270, the map creating unit 252, and the process executing unit 256. The OCT scanner 270 is configured to acquire the first three dimensional data set and the second three dimensional data set by applying OCT scans to the sample (the eye 120). The map creating unit 252 is configured to create the first two dimensional map based on representative intensity values of a plurality of pieces of A-scan data included in the first three dimensional data set. Further, the map creating unit 252 is configured to create the second two dimensional map based on representative intensity values of a plurality of pieces of A-scan data included in the second three dimensional data set. The process executing unit 256 is configured to execute a process based on at least one of at least the first partial data set of the first three dimensional data set and at least the second partial data set of the second three dimensional data set, based on the first two dimensional map and the second two dimensional map.

According to the ophthalmic apparatus 150 thus configured, the process based on two (or more) three dimensional data sets can be performed using the two dimensional maps created from the three dimensional data sets acquired by OCT scans. Therefore, processing of OCT data acquired from the sample can be performed without having to perform the three dimensional image construction and/or the landmark detection (landmark identification) as in the invention described in U.S. Pat. Nos. 7,884,945 and 8,405,834. This makes it possible to improve effective utilization of resources required for processing and shorten processing time, thereby achieving further efficiency improvement in OCT data processing. Consequently, real-time processing can be preferably performed, for example.

In the ophthalmic apparatus 150 of the present aspect, the process executing unit 256 may include the analyzing unit 2561. The analyzing unit 2561 is configured to perform a predetermined analysis process based on at least one of at least the first partial data set of the first three dimensional data set and at least the second partial data set of the second three dimensional data set, based on the first two dimensional map and the second two dimensional map.

According to such a configuration, an analysis of OCT data acquired from the sample can be performed without having to perform the three dimensional image construction and/or the landmark detection (landmark identification) as in the conventional technology. This makes it possible to improve effective utilization of resources required for analysis and shorten processing time, thereby achieving further efficiency improvement in analysis. Consequently, real-time analysis can be preferably performed, for example.

In the ophthalmic apparatus 150 of the present aspect, the process executing unit 256 may include the evaluating unit 2562. The evaluating unit 2562 is configured to execute a predetermined evaluation process based on the analysis data obtained by the analyzing unit 2561, based on the first two dimensional map and the second two dimensional map.

According to such a configuration, an evaluation on a desired region of the sample can be performed without having to perform the three dimensional image construction and/or the landmark detection (landmark identification) as in the conventional technology. This makes it possible to improve effective utilization of resources required for evaluation and shorten processing time, thereby achieving further efficiency improvement in evaluation. Consequently, real-time evaluation can be preferably performed, for example.

In the ophthalmic apparatus 150 of the present aspect, the process executing unit 256 may include the ROI setting unit 2563. The ROI setting unit 2563 is configured to set a region(s) of interest (e.g., an analysis target region(s) and/or an evaluation target region(s)) in the first three dimensional data set and/or the second three dimensional data set, based on the first two dimensional map and the second two dimensional map.

According to such a configuration, a region of interest can be set without having to perform the three dimensional image construction and/or the landmark detection (landmark identification) as in the conventional technology. This makes it possible to improve effective utilization of resources required for setting a region of interest and shorten processing time, thereby achieving further efficiency improvement in setting of a region of interest. Consequently, the region of interest can be preferably set in real-time, for example.

In the ophthalmic apparatus 150 of the present aspect, the process executing unit 256 may include the examination area setting unit 2564. The examination area setting unit 2564 is configured to set a predetermined area to which examination is applied (examination area) for the sample, based on the first two dimensional map and the second two dimensional map.

According to such a configuration, an examination area can be set without having to perform the three dimensional image construction and/or the landmark detection (landmark identification) as in the conventional technology. This makes it possible to improve effective utilization of resources required for setting an examination area and shorten processing time, thereby achieving further efficiency improvement in setting of an examination area. Consequently, the examination area can be preferably set in real-time, for example.

In the ophthalmic apparatus 150 of the present aspect, the process executing unit 256 may include the imaging area setting unit 2565. The imaging area setting unit 2565 is configured to set a partial data set to which a predetermined imaging process is applied (an imaging area), based on the first two dimensional map and the second two dimensional map.

According to such a configuration, an imaging area can be set without having to perform the three dimensional image construction and/or the landmark detection (landmark identification) as in the conventional technology. This makes it possible to improve effective utilization of resources required for setting an imaging area and shorten processing time, thereby achieving further efficiency improvement in setting of an imaging area. Consequently, the imaging area can be preferably set in real-time, for example.

The ophthalmic apparatus 150 of the present aspect may include a device for preparing examination data acquired from the sample by a predetermined examination that is different from OCT. The examination data preparing device includes, for example, a device of receiving examination data (the receiving unit 190) or a device of acquiring examination data by applying examination to the sample. Furthermore, the process executing unit 256 may include the comparing unit 2567. The comparing unit 2567 is configured to execute a predetermined comparison process between the examination data and at least part of the three dimensional data set, based on the first two dimensional map and the second two dimensional map.

According to such a configuration, the comparison process between the examination data and the OCT data can be carried out without having to perform the three dimensional image construction and/or the landmark detection (landmark identification) as in the conventional technology. This makes it possible to improve effective utilization of resources required for the comparison process and shorten processing time, thereby achieving further efficiency improvement in the comparison process. Consequently, the comparison process can be preferably performed in real-time, for example.

In the ophthalmic apparatus 150 of the present aspect, the process executing unit 256 may include the registration unit 2568. The registration unit 2568 is configured to perform registration between at least the first partial data set and at least the second partial data set, via registration between the first two dimensional map and the second two dimensional map.

According to such a configuration, registration between two (or more) pieces of OCT data can be performed without having to perform the three dimensional image construction and/or the landmark detection (landmark identification) as in the conventional technology. This makes it possible to improve effective utilization of resources required for the registration and shorten processing time, thereby achieving further efficiency improvement in the registration. Consequently, the registration can be preferably performed in real-time, for example.

In the ophthalmic apparatus 150 of the present aspect, the process executing unit 256 may include the registration unit 2569. The registration unit 2569 is configured to perform adjustment of an area to which an OCT scan for the sample is applied, via registration between the first two dimensional map and the second two dimensional map.

Furthermore, the ophthalmic apparatus 150 according to the present aspect can perform tracking according to the movement of the sample (tracking for chasing after the moving sample). The tracking can be achieved by the process executing unit 256 (the registration unit 2569) that sequentially processes three dimensional data sets sequentially acquired from the sample and by sequential performance of adjustments of the area to which OCT scans are applied for the sample.

According to such a configuration, tracking according to the movement of the sample can be performed without having to perform the three dimensional image construction and/or the landmark detection (landmark identification) as in the conventional technology. This makes it possible to improve effective utilization of resources required for tracking and shorten processing time, thereby achieving further efficiency improvement in tracking. Consequently, the tracking can be preferably performed in real-time, for example.

In the process executed by the process executing unit 256 of the ophthalmic apparatus 150 of the present aspect, the registration between the first two dimensional map and the second two dimensional map (in particular, the comparison of the two dimensional maps) may include an image correlation calculation. The image correlation calculation may be performed to determine a positional difference amount between the first two dimensional map and the second two dimensional map. The registration may be performed between the first two dimensional map and the second two dimensional map based on the positional difference amount derived using the image correlation calculation. The positional difference amount may include at least one of a translation amount and a rotation amount.

According to such a configuration, the relative positional relationship between two dimensional maps can be obtained in an effective manner using the image correlation (typically, phase only correlation) without having to go through a process that requires many resources such as the landmark detection (landmark identification).

The first three dimensional data set and the second three dimensional data set acquired by the ophthalmic apparatus 150 of the present aspect may be acquired from mutually different three dimensional regions of the sample. If this is the case, the process executing unit 256 may perform composition of the first image data generated from at least the first partial data set and the second image data generated from at least the second partial data set, via registration between the first two dimensional map and the second two dimensional map.

According to such a configuration, the composition of a plurality of pieces of image data corresponding to a plurality of mutually different regions of the sample can be performed in an effective manner without having to go through a process that requires many resources such as the landmark detection (landmark identification).

As described above, the sample of the present aspect is a living eye, but any OCT apparatus used for measurement of samples other than living eyes may have the same and/or like functions and configurations. In other words, any of the matters (e.g., functions, hardware configurations, software configurations, etc.) regarding the ophthalmic apparatus 150 may be combined with an OCT apparatus of any aspect. The matters combined yield or provide actions and effects accordingly.

Some exemplary aspects relate to a method of controlling an OCT apparatus that includes a processor and an OCT scanner that applies an OCT scan to a sample. The control method may include at least the following steps: a step of controlling the OCT scanner to acquire the first three dimensional data set and the second three dimensional data set from the sample; a step of controlling the processor to create the first two dimensional map based on representative intensity values of a plurality of pieces of A-scan data included in the first three dimensional data set; a step of controlling the processor to create the second two dimensional map based on representative intensity values of a plurality of pieces of A-scan data included in the second three dimensional data set; and a step of controlling the processor to execute a process based on at least one of at least the first partial data set of the first three dimensional data set and at least the second partial data set of the second three dimensional data set, based on the first two dimensional map and the second two dimensional map.

Any of the matters (e.g., functions, hardware configurations, software configurations, etc.) regarding the ophthalmic apparatus 150 may be combined with the control method of the present aspect. The matters combined yield or provide actions and effects accordingly.

Some exemplary aspects relate to a program that causes a computer to execute such a control method of the OCT apparatus. Any of the matters described regarding the ophthalmic apparatus 150 may be combined with the program. Further, some exemplary aspects relate to a computer-readable non-transitory recording medium storing such a program. Any of the matters described regarding the ophthalmic apparatus 150 may be combined with the recording medium.

Some exemplary aspects relate to an apparatus for processing data acquired using OCT (OCT data processing apparatus). The OCT data processing apparatus may include at least the following elements: a receiving unit that receives the first three dimensional data set and the second three dimensional data set acquired by applying OCT scans to a sample; a map creating unit that creates the first two dimensional map based on representative intensity values of a plurality of pieces of A-scan data included in the first three dimensional data set, and creates the second two dimensional map based on representative intensity values of a plurality of pieces of A-scan data included in the second three dimensional data set; and a process executing unit that executes a process based on at least one of at least the first partial data set of the first three dimensional data set and at least the second partial data set of the second three dimensional data set, based on the first two dimensional map and the second two dimensional map.

In other words, the OCT data processing apparatus is an apparatus that includes an element (a receiving unit) that receives a three dimensional data set acquired by an OCT scan from the outside (e.g., an OCT apparatus, an image archiving system, a recording medium), in place of or in addition to the OCT scanner 270 of the OCT apparatus (the ophthalmic apparatus) 150 described above. The receiving unit may include a communication device or a drive device, for example.

Any of the matters (e.g., functions, hardware configurations, software configurations, etc.) regarding the ophthalmic apparatus 150 may be combined with the OCT data processing apparatus of the present aspect. The matters combined yield or provide actions and effects accordingly.

Some exemplary aspects relate to a method of controlling an OCT data processing apparatus that includes a processor. The control method may include at least the following steps: a step of controlling the processor to receive the first three dimensional data set and the second three dimensional data set acquired by applying OCT scans to a sample; a step of controlling the processor to create the first two dimensional map based on representative intensity values of a plurality of pieces of A-scan data included in the first three dimensional data set; a step of controlling the processor to create the second two dimensional map based on representative intensity values of a plurality of pieces of A-scan data included in the second three dimensional data set; and a step of controlling the processor to execute a process based on at least one of at least the first partial data set of the first three dimensional data set and at least the second partial data set of the second three dimensional data set, based on the first two dimensional map and the second two dimensional map.

Any of the matters (e.g., functions, hardware configurations, software configurations, etc.) regarding the ophthalmic apparatus 150 may be combined with the control method of the present aspect. The matters combined yield or provide actions and effects accordingly.

Some exemplary aspects relate to a program that causes a computer to execute such a control method of the OCT data processing apparatus. Any of the matters described regarding the ophthalmic apparatus 150 may be combined with the program. Further, some exemplary aspects relate to a computer-readable non-transitory recording medium storing such a program. Any of the matters described regarding the ophthalmic apparatus 150 may be combined with the recording medium.

An OCT apparatus (e.g., the ophthalmic apparatus 150) of some exemplary aspects, a control method of an OCT apparatus of some exemplary aspects, an OCT data processing apparatus of some exemplary aspects, or a control method of an OCT data processing apparatus of some exemplary aspects provides a method of processing OCT data. Such an OCT data processing method may include at least the following steps: a step of preparing the first three dimensional data set and the second three dimensional data set acquired from a sample; a step of creating the first two dimensional map based on representative intensity values of a plurality of pieces of A-scan data included in the first three dimensional data set; a step of creating the second two dimensional map based on representative intensity values of a plurality of pieces of A-scan data included in the second three dimensional data set; and a step of executing a process based on at least one of at least the first partial data set of the first three dimensional data set and at least the second partial data set of the second three dimensional data set, based on the first two dimensional map and the second two dimensional map.

Any of the matters (e.g., functions, hardware configurations, software configurations, etc.) regarding the ophthalmic apparatus 150 may be combined with the OCT data processing method of the present aspect. The matters combined yield or provide actions and effects accordingly.

Some exemplary aspects relate to a program that causes a computer to execute such an OCT data processing method. Any of the matters described regarding the ophthalmic apparatus 150 may be combined with the program. Further, some exemplary aspects relate to a computer-readable non-transitory recording medium storing such a program. Any of the matters described regarding the ophthalmic apparatus 150 may be combined with the recording medium.

In some aspects, the non-transitory recording medium on which the program is recorded may be in any form, and examples thereof include a magnetic disk, an optical disk, a magneto-optical disk, a semiconductor memory, and the like.

While certain embodiments have been described, these embodiments have been presented by way of example only, and are not intended to limit the scope of the inventions. Indeed, the novel embodiments described herein may be embodied in a variety of other forms; furthermore, various omissions, substitutions, additions and changes in the form of the embodiments described herein may be made without departing from the spirit of the inventions. The accompanying claims and their equivalents are intended to cover such forms or modifications as would fall within the scope and spirit of the inventions.

What is claimed is:

1. A method of processing data acquired by applying an optical coherence tomography (OCT) scan to a sample in a system including an OCT scanner and an OCT data processor, the method comprising:
   preparing, using the OCT data processor, a three dimensional data set acquired from a sample by the OCT scanner, the three dimensional data set being data before being subjected to an imaging process;
   creating, using the OCT data processor, a two dimensional map based on representative intensity values of a plurality of pieces of A-scan data included in the three dimensional data set;
   placing, using the OCT data processor, the three dimensional data set based on the two dimensional map; and
   executing a process using the OCT data processor based on at least a partial data set of the three dimensional data set on which placement based on the two dimensional map has been performed.

2. The OCT data processing method of claim 1, wherein the process includes an analysis process.

3. The OCT data processing method of claim 2, wherein the process includes an evaluation process based on data obtained by the analysis process.

4. The OCT data processing method of claim 2, wherein the process includes setting of a partial data set to which the analysis process is applied.

5. The OCT data processing method of claim 1, wherein the process includes setting of an area to which an examination for the sample is applied.

6. The OCT data processing method of claim 1, wherein the process includes setting of a partial data set to which an imaging process is applied.

7. The OCT data processing method of claim 1, further comprising preparing examination data acquired from the sample by an examination different from OCT, wherein
   the process includes a comparison process between the examination data and at least part of the three dimensional data set.

8. A method of processing data acquired by applying an optical coherence tomography (OCT) scan to a sample in a system including an OCT scanner and an OCT data processor, the method comprising:
   preparing, using the OCT data processor, a first three dimensional data set and a second three dimensional data set acquired from a sample by the OCT scanner, the first and second three dimensional data sets being data before being subjected to an imaging process;
   creating, using the OCT data processor, a first two dimensional map based on representative intensity values of a plurality of pieces of A-scan data included in the first three dimensional data set;
   creating, using the OCT data processor, a second two dimensional map based on representative intensity values of a plurality of pieces of A-scan data included in the second three dimensional data set; and
   executing a process using the OCT data processor based on at least one of at least a first partial data set of the first three dimensional data set and at least a second partial data set of the second three dimensional data set, based on the first two dimensional map and the second two dimensional map.

9. The OCT data processing method of claim 8, wherein the process includes registration between the at least the first partial data set and the at least the second partial data set via registration between the first two dimensional map and the second two dimensional map.

10. The OCT data processing method of claim 8, wherein the process includes adjustment of an area to which an OCT scan for the sample is applied via registration between the first two dimensional map and the second two dimensional map.

11. The OCT data processing method of claim 10, wherein the adjustment is sequentially performed by sequentially processing three dimensional data sets sequentially acquired from the sample.

12. The OCT data processing method of claim 9, wherein the registration between the first two dimensional map and the second two dimensional map includes an image correlation calculation.

13. The OCT data processing method of claim 12, wherein
   the image correlation calculation is performed to determine a positional difference amount between the first two dimensional map and the second two dimensional map, and
   the registration between the first two dimensional map and the second two dimensional map is performed based on the positional difference amount.

14. The OCT data processing method of claim 13, wherein the positional difference amount includes at least one of a translation amount and a rotation amount.

15. The OCT data processing method of claim 8, wherein
   the first three dimensional data set and the second three dimensional data set are acquired from mutually different three dimensional regions of the sample, and
   the process includes composition of first image data generated from the at least the first partial data set and second image data generated from the at least the second partial data set via registration between the first two dimensional map and the second two dimensional map.

16. The OCT data processing method of claim 8, wherein the process includes an analysis process.

17. The OCT data processing method of claim 16, wherein the process includes an evaluation process based on data obtained by the analysis process.

18. The OCT data processing method of claim 16, wherein the process includes setting of a partial data set to which the analysis process is applied.

19. The OCT data processing method of claim 16, further comprising preparing a plurality of three dimensional data sets respectively corresponding to a plurality of different time points, the plurality of three dimensional data sets including the first three dimensional data set and the second three dimensional data set, wherein
the analysis process includes a process of determining a time course of a parameter value.

20. An optical coherence tomography (OCT) data processing apparatus comprising:
an OCT scanner; and
an OCT data processor including
a receiver that receives a three dimensional data set acquired by applying an OCT scan to a sample by the OCT scanner, the three dimensional data set being data before being subjected to an imaging process;
map creating circuitry that creates a two dimensional map based on representative intensity values of a plurality of pieces of A-scan data included in the three dimensional data set;
placing circuitry that performs placement of the three dimensional data set based on the two dimensional map; and
process executing circuitry that executes a process based on at least a partial data set of the three dimensional data set on which the placement has been performed.

* * * * *